United States Patent

Thibault et al.

[19]

[11] Patent Number: 5,520,061

[45] Date of Patent: May 28, 1996

[54] MULTIPLE AXIS TRANSDUCER MOUNTING COLLAR

[75] Inventors: Scott E. Thibault, Schenectady; William H. Miller, Loudonville, both of N.Y.; Warren R. Brook, Medford, N.J.; Timothy P. Mannix, Cincinnati, Ohio

[73] Assignee: Enprotech Corporation, New York, N.Y.

[21] Appl. No.: 107,326

[22] Filed: Aug. 16, 1993

Related U.S. Application Data

[63] Continuation-in-part of Ser. No. 798,203, Nov. 26, 1991, abandoned, which is a continuation-in-part of Ser. No. 584,893, Sep. 19, 1990, Pat. No. 5,068,800, and a continuation-in-part of Ser. No. 585,884, Sep. 19, 1990, Pat. No. 5,159,563, which is a continuation-in-part of Ser. No. 323,313, Mar. 14, 1989, Pat. No. 4,975,855.

[51] Int. Cl.⁶ .............. G01N 29/12; G01N 29/26
[52] U.S. Cl. .............. 73/866.5; 73/622; 73/579; 73/660
[58] Field of Search .............. 73/866.5, 620, 73/622, 625, 579, 628, 641, 650, 659, 660

[56] References Cited

U.S. PATENT DOCUMENTS

| | | | |
|---|---|---|---|
| 3,411,344 | 11/1968 | Lloyd | 73/622 |
| 3,555,894 | 1/1971 | Bratkowski | 73/88.5 |
| 4,213,346 | 7/1980 | Polovnikov et al. | 73/660 |
| 4,283,952 | 8/1981 | Newman | 73/579 |
| 4,302,813 | 11/1981 | Kurihara et al. | 364/508 |
| 4,546,425 | 10/1985 | Breitholtz | 364/153 |
| 4,561,306 | 12/1985 | Marino et al. | 73/432 R |
| 4,790,191 | 12/1988 | Shultz, Jr. | 73/661 |
| 4,805,457 | 2/1989 | Oates et al. | 73/660 |
| 4,817,417 | 4/1989 | Twerdochlib | 73/660 |
| 4,829,823 | 5/1989 | Michel | 73/579 |
| 4,941,105 | 7/1990 | Marangoni | 73/660 |
| 4,957,000 | 9/1990 | Delpy et al. | 73/622 |
| 4,975,855 | 12/1990 | Miller et al. | 364/507 |
| 5,062,296 | 11/1991 | Migliori | 73/579 |

OTHER PUBLICATIONS

Kistler Instrument Corporation Product Catalog, pp. 42 and 49.

*Primary Examiner*—Hezron E. Williams
*Assistant Examiner*—Rose M. Finley
*Attorney, Agent, or Firm*—Heslin & Rothenberg

[57] ABSTRACT

An improved apparatus and method for determining the existence and severity of a crack in a shaft system is provided. The apparatus includes means for mounting multiple vibration responsive output transducers around an outer circumference of the shaft system, allowing simultaneous measurements of vibrational response of the shaft system when multiple vibration responsive output transducers are mounted to the mounting means. In a first approach, the mounting means comprises a collar having two connected arcuate members, with drilled milled and tapped apertures for mounting radial input and output transducers. Torsional input and output transducers may also be mounted tangentially on the collar in drilled milled and tapped heads of bolts used to connect the two arcuate members. In a second approach, the mounting means comprises a plurality of support blocks disposed substantially symmetrically around and protruding outward from the outer collar circumference with each of the blocks orienting at least one transducer in a radial direction and at least one transducer in a tangential direction. Each block may further orient another transducer in an axial direction.

51 Claims, 27 Drawing Sheets

5,520,061

MULTIPLE AXIS TRANSDUCER MOUNTING COLLAR

CROSS REFERENCE TO RELATED APPLICATIONS

This application is a continuation-in-part of U.S. Ser. No. 798,203, filed Nov. 26, 1991, now abandoned which was a continuation-in-part of U.S. Ser. No. 584,893, filed Sep. 19, 1990, now U.S. Pat. No. 5,068,800, issued Nov. 26, 1991, and U.S. Ser. No. 585,884, filed Sep. 19, 1990, now U.S. Pat. No. 5,159,563, issued Oct. 27, 1992, each of which is a continuation-in-part of U.S. Ser. No. 323,313, filed Mar. 14, 1989, now U.S. Pat. No. 4,975,855, issued Dec. 4, 1990, the contents of each of which are hereby incorporated by reference into this application.

FIELD OF THE INVENTION

This invention relates in general to the field of non-destructive testing and more particularly to a collar for use in determining the presence, size and location of a crack in a shaft.

BACKGROUND OF THE INVENTION

For the purposes of this description, a crack is defined as any non-designed physical discontinuity and the term shaft encompasses any axially extending structure which has a length considerably larger than its cross sectional dimension. Such structures take a wide variety of forms and are employed as motor rotors, shafts of pumps, generators, compressors and turbines, bolts and other fasteners, piping, etc. Although the present invention is applicable to any such structures, it will be presented, by way of example, in the context of detecting a crack in a reactor coolant pump shaft of a pressurized water reactor (PWR). Other examples would include boiling water reactor (BWR) recirculation pumps.

Nuclear reactors have been operating and producing useful electricity for many years. Within the last few years, several plants have found cracks in the reactor coolant pump shaft near the thermal barrier.

The large reactor coolant pump of a PWR circulates water out of the reactor vessel into steam generators which in turn pass steam to a steam turbine. The reactor coolant pump system consists of a vertical pump with a vertical motor mounted on the pump from above. In a typical design, the entire shaft system hangs vertically and is supported by a thrust bearing located on the top of the vertical motor. The pump system usually has an overhung impeller and an axial suction inlet from below the pump. The cooling water exits the pump through a single radial discharge in the horizontal direction. A net radial force is developed on the rotating shaft during the operation of the pump. This unidirectional unbalanced force applied to the rotating pump shaft has lead to fatigue cracks in the shaft and subsequent pump shaft failure for some pump designs.

The consequences of an unforeseen pump shaft failure can be severe. A nuclear facility can lose millions of dollars a day in revenues from an unscheduled outage. Since pump shaft replacement is an expensive, time consuming project, it is highly desirable to be able to discover the crack condition early and thus have time to plan and schedule the replacement.

In co-assigned U.S. Pat. No. 4,975,855, issued Dec. 4, 1990 (Miller et al.), the entire contents of which are hereby incorporated by reference, the presence, size and location of a crack in a shaft is determined by comparing actual measured natural frequencies of the shaft with the results of an analytical model. From a multistation analytical model of an uncracked shaft, natural frequencies and associated mode shapes are derived. A suspected axial location of a crack is defined and a natural frequency of interest is selected which has an associated mode shape exhibiting significant localized bending at the suspected axial location of the crack and a site of response measurement. The analytical model is modified to include a representation of a radial crack at the probable axial location, and the predicted split and downward shift of the natural frequency of interest as a function of crack depth is calculated from the modified model. The actual shaft is subjected to a radial excitation force, and vibrational response measurements are taken with a single accelerometer diametrically opposite the input transducer. Measurements are taken sequentially along multiple radial directions. A fast Fourier transform analyzer derives a frequency response function from the measurements for each radial direction. The frequency response functions indicate the actual natural frequencies of the shaft. A comparison of these actual natural frequencies with those predicted by the modified model is employed to determine the presence and severity of a crack in the shaft.

Earlier collars mounted only one input and a diametrically opposed output transducer for radial testing. This required the test technician to loosen the collar and rotate the shaft, or if that was not possible, to rotate the collar and move the shaker position to establish a new radial excitation direction. The collar/shaft rotation should ideally be 45° for each radial test direction. However, the access to the coupling on all of the pumps to date is very limited, allowing only a ±27.5° rotation of the collar. The shaft systems on most major machines are too massive to allow for the rotation of the shaft. As a result of this limitation, only three radial directions were capable of being tested utilizing the previous collars. This left a rather large gap in the test data. Also, there have been tests where the test shaft was resting against a bearing in one of the test directions, making the data from that one direction almost useless.

A need thus exists for a means of putting energy into and measuring energy from the shaft under test at multiple locations around the entire circumference of the shaft. This means should be easy to install, make no permanent marks to the shaft, and allow for quick, efficient, and accurate recording of the input and output energies.

SUMMARY OF THE INVENTION

This need is satisfied and the deficiencies of the prior art overcome, in accordance with the principles of the present invention, through the use of a collar which makes use of modal analysis techniques which have been based on the modal theory of reciprocity. Frequency response functions can be accurately measured in multiple directions utilizing only one energy input direction. The major advantage of the collar provided by the subject invention is the ability to record data from multiple radial, tangential, or axial directions without the need to rotate the shaft or the collar. Rotating the collar requires repositioning the shaker as well. The collar of the subject invention eliminates this requirement, thereby saving time, and also reduces the risk of damaging the sensitive test equipment.

The collar preferably comprises a first arcuate member having two ends and a second arcuate member having two ends. The first arcuate member is connected to the second arcuate member such that the inner circumference of the connected members approximates the outer circumference of a shaft to be measured for vibrational response. The collar further includes means for mounting multiple vibration responsive output transducers on the connected members.

According to a first approach, the means for mounting the multiple vibration responsive output transducers comprises drilled milled tapped apertures in the connected arcuate members. Output transducers are mounted in each of the drilled milled tapped apertures. The transducers which are mounted 180° from each other, theoretically, should contain redundant data (also based on the modal theory of reciprocity). However, it has been verified that when one radial direction contains marginal data due to the shaft touching a bearing, the transducer mounted 180° opposite that one radial direction may contain good data. Therefore, one collar according to the subject invention contains transducers at every 45° completely around the circumference of the collar for a total of eight output transducers.

Furthermore, the new collar provides for measurements for both radial and torsional testing. For torsional testing, the input transducer is mounted tangentially at a circumferential location on the collar, and the output transducer is mounted at a circumferential location displaced 180 degrees from the location of the input transducer mounting.

Preferably, the torsional input transducer and the torsional output transducer are mounted in the heads of bolts used to connect the two arcuate members of the collar together. For ease in attaching the collar around the shaft to be tested, the bolts may be premounted to one of the arcuate members.

In one case, two collars of the subject invention are utilized simultaneously for radial and torsional testing, with one collar being mounted on the spool of the reactor coolant pump and the other collar being mounted on the hub of the reactor coolant pump. However, in other cases, as with a collar according to a second approach described below, both collars may be mounted on the spool of the pump.

Also provided by the subject invention is a method of measuring vibrational response of a shaft system under test which comprises selecting an axial site of vibration response measurement on the shaft system. An excitation force is then introduced to the shaft system, and simultaneous measurements at the axial site of vibrational response of the shaft system to the excitation force are taken. The simultaneous measurements are taken at multiple locations around the outer circumference of the shaft system. This is preferably accomplished using the collar of the subject invention, which allows multiple output transducers to be mounted around the entire circumference of the shaft.

According to a second approach, the means for mounting the multiple vibration responsive output transducers comprises a plurality of support means disposed substantially symmetrically around the outer collar circumference with each of the support means having a first means for orienting at least one transducer in a first direction and a second means for orienting at least one transducer in a second direction that is substantially orthogonal to the first direction. Each of the support means may further comprise a third means for orienting at least one transducer in a third direction that is substantially orthogonal to both the first and second directions. In one case, the first direction is a radial direction, the second direction is a tangential direction, and the third direction is an axial direction.

Preferably, the support means protrude outward from the outer circumference of the collar a distance greater than the minimum radial thickness of either the first or second arcuate member. In one case, the support means are blocks each having one face adjoining the collar and having relatively large mass in comparison to that portion of the collar which supports each such block. Each block has an input or output transducer mounted on a radially, tangentially, or axially-facing face of the block. Input transducers may be mounted on the support means in place of output transducers as needed for a particular testing configuration. In general, an input transducer may be mounted on a support means with an orientation in the first, second, or third directions above.

The collar preferably has substantial symmetry with respect to mass and stiffness and is sufficiently rigid to substantially prevent vibrational noise caused by collar deformation or by relative motion between the collar and the shaft. Also, the first and second arcuate members of the collar are preferably substantially equal-sized and an inner circumference of each arcuate member approximates 180 degrees of the outer circumference of the shaft. A connecting bolt having a threaded end, for mating with a tapped aperture which is disposed on at least one end of either the first or second arcuate member, is preferably used to connect the first and second arcuate members. Tangential input or output transducers may be mounted in either the head or the threaded end of the connecting bolt so that all tangential transducers used for testing may be mounted to be in-phase.

BRIEF DESCRIPTION OF THE FIGURES

These and other objects, features and advantages of this invention will be evident from the following detailed description of preferred embodiments when read in conjunction with the accompanying drawings in which.

DETAILED DESCRIPTION OF THE INVENTION

Figure 1:
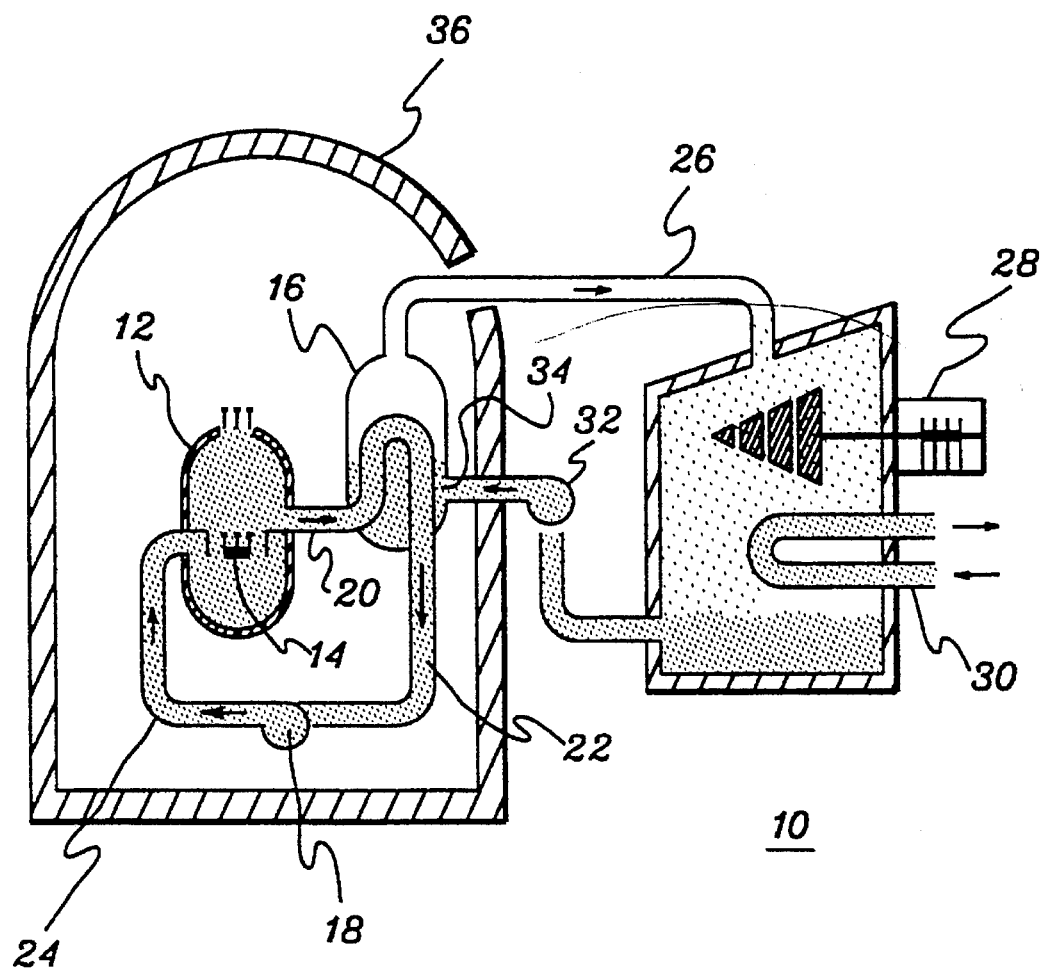
FIG. 1 is a simplified schematic representation of a typical pressurized water reactor (PWR) nuclear power plant.

A schematic of a typical pressurized water reactor (PWR) nuclear power plant 10 is shown in FIG. 1. In operation, high temperature, high pressure water is pumped from the reactor vessel 12 (from around the reactor core 14) to a steam generator (heat exchanger) 16 by the reactor coolant pump 18. A continuous loop of piping 20,22,24 interconnects the pressure vessel 12, steam generator 16 and reactor coolant pump 18, as shown. Steam generator 16 in turn passes steam along steam line 26 to a steam turbine generator 28. Finally, cooling water from a condenser 30 is pumped by pump 32 into the inlet of 34 of steam generator 16.

Figure 2:
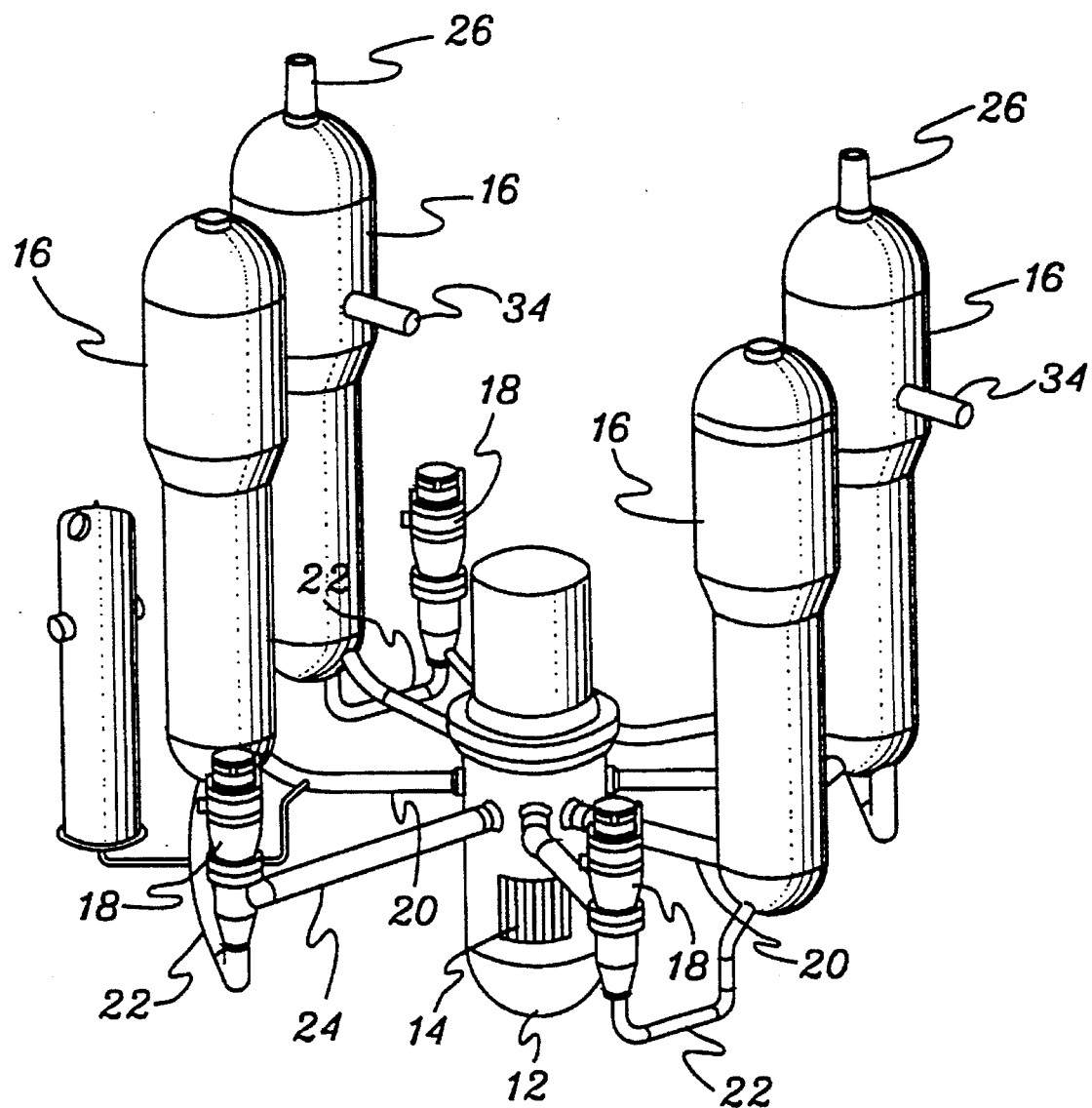
FIG. 2 is a more detailed illustration of a reactor coolant system for a PWR.
Figure 3:
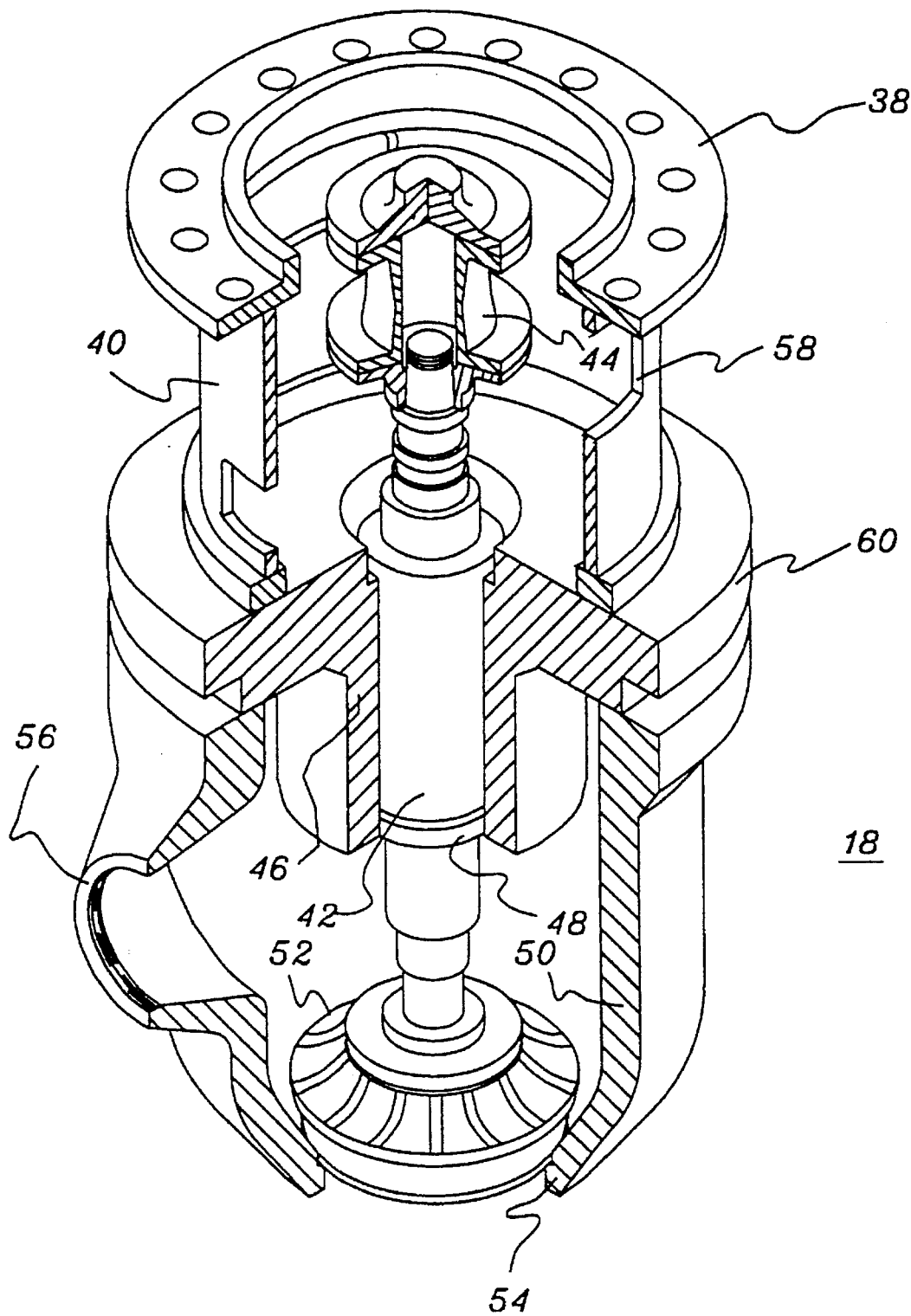
FIG. 3 is a partially broken away sectional view of a typical reactor coolant pump.

FIG. 2 is a more detailed sketch of the reactor coolant system for the PWR which is housed inside the containment structure 36. Four reactor coolant pumps (RCPs) 18 and associated steam generators 16 surround and are interconnected with the reactor vessel 12. If one of the RCPs 18 should fail and be shut down because of a crack in the pump shaft, the nuclear power plant may still be able to operate but obviously at a reduced load and with significantly reduced revenue generated. FIG. 3 is a sectional, partially broken away view of a typical reactor coolant pump. A drive motor (not shown) is mounted on flange 38 atop motor support housing 40. The motor's rotor is connected to the pump shaft 42 by a spool piece coupling 44. A radial guide bearing 46 surrounds a portion of pump shaft 42 at a location above a thermal barrier 48. Thermal barrier 48 serves to isolate the bearing area from the extremely high temperatures of the water within the casing 50. An impeller 52 is mounted at the lower end of shaft 42 by a set of bolts (not shown).

Water from the steam generator enters vertically upward into the suction nozzle 54 of the reactor coolant pump 18. The pump discharge is horizontal through discharge nozzle 56 into the reactor vessel. During operation of the pump, discharge flow causes a net pressure differential across the pump shaft 42. Since the pump shaft is rotating in the pump casing 50, a given point on the shaft is subjected to a cyclic force. This force is reacted by the pump shaft 42 on the guide bearing 46. Generally, the thermal barrier and the guide bearing journal have a sleeve shrunk on the shaft at these locations. In some cases, the sleeve is further secured through the use of a shear pin, or welding, or both locking mechanisms (not shown). The shear pin and welding give rise to stress concentrations which in combination with the cyclic force can result in the formation of a shaft crack, often just below the thermal barrier. Continued operation of the pump will cause the crack to propagate. Shaft cracks have occurred in operating nuclear power plants and have apparently gone undetected until the pump impeller 52 broke off the shaft 42.

The shaft crack detection method disclosed in U.S. Pat. No. 4,975,855 was developed in order to identify the presence, size and location of a vertical reactor coolant pump shaft crack. The method recognized that the only access to the shaft system was through the cutouts 58 in the motor support housing 40 which was mounted on the main flange 60 and enclosed the coupling 44. No other access to the pump shaft 42 was, or currently is, readily available. The method enabled both the excitation to the shaft 42, and the response to be obtained through the motor stand access holes 58, without any disassembly.

Figure 4:
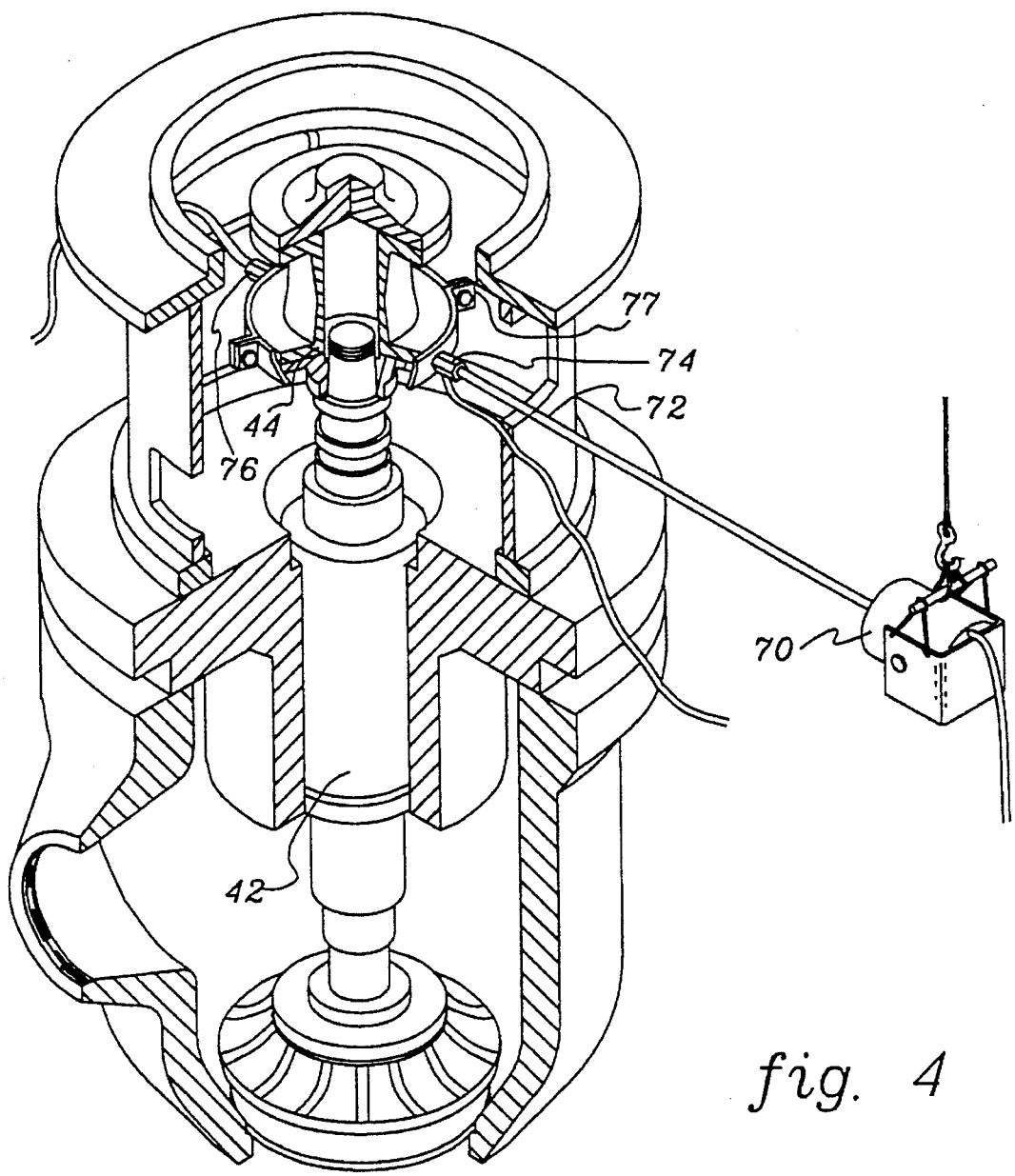
FIG. 4 is a partially cut-away sectional view of a typical reactor coolant pump shaft test instrumentation arrangement for measuring radial vibrational response of the pump shaft.

FIG. 4 illustrates prior exemplary test equipment used to measure the actual natural frequencies of shaft 42 of the RCP. The shaft is excited radially using an electromagnetic shaker 70 connected to the coupling 44 by a stinger 72 (i.e. a thin cylindrical rod). A load cell 74 (also referred to herein as an input transducer) measures the input force and provides an electrical signal representation thereof. The radial vibrational response of the shaft is measured by an accelerometer 76 located diametrically opposite from the stinger 72. A rotatable collar 77, to which load cell 74 and accelerometer 76 are attached, is employed to change the radial direction of measurement.

The output signals from accelerometer 76 and load cell 74 are fed through suitable couplers to an FFT analyzer. The analyzer, in known fashion, provides a frequency response function, the peaks of which represent the actual natural frequencies. By exciting the shaft and measuring the system response in limited predetermined radial directions around the shaft, the variation of the shaft natural frequencies as a function of circumferential position is observed.

According to a first approach, the subject invention provides for excitation of the shaft and measurement of system responses at radial directions around the complete circumference of the shaft, without the limitations of the prior method. In one preferred embodiment, an excitation force is introduced at an excitation site on a shaft system under test and measurements are taken of the shaft system vibrational response along multiple radial directions for radial analysis and/or a tangential direction for torsional analysis. The measurements are processed, preferably by a fast Fourier transform analyzer, to determine the actual natural frequency(s) of the shaft system in the region of frequency of interest. A correlation between the actual natural frequency(s) and the shift and split in the radial analysis natural frequency of interest and/or the shift in the torsional analysis natural frequency of interest predicted by the analytical model, provides an indication of shaft crack presence and severity. Torsional analysis requires only a single vibrational response measurement to determine the presence and depth of a crack; radial analysis affords an indication of the circumferential location of a shaft crack. A complete discussion of the radial analysis of natural frequencies, once obtained using the present invention, can be found in co-assigned U.S. Pat. No. 4,975,855, issued Dec. 4, 1990. A complete discussion of the torsional analysis as well as radial analysis of natural frequencies, once obtained using the present invention, can be found in co-assigned U.S. Pat. No. 5,068,800, issued Nov. 26, 1991, and co-assigned U.S. Pat. No. 5,159,563, issued Oct. 27, 1992. The contents of each of these disclosures is incorporated herein.

Briefly, the analysis is based on the observation that there is a direct correlation between the existence of a crack and the crack's effect on the shaft system's lateral (also referred to herein as radial) and torsional natural frequencies. A given shaft system will have a series of natural or resonant frequencies. If an asymmetric crack is introduced into the shaft, each of the radial natural frequencies splits into two new, different lower frequencies. The lowest of the new frequencies is associated with a soft axis which extends along the depth of the crack; the other new frequency is associated with a stiff axis substantially parallel to the wave front of the crack. The reduction in value of radial natural frequency and the separation between the two new frequencies can be correlated with the depth of the crack. The circumferential position of the crack can be determined by taking readings in multiple radial directions.

When an asymmetric crack is introduced into the shaft, each of the torsional natural frequencies shifts to a different lower frequency. The reduction in value of torsional natural frequencies can be correlated with the depth of the crack.

The collars provided by the subject invention allow for multiple output transducers (accelerometers) to be mounted around the complete circumference of the shaft under test, and output measurements to be taken simultaneously without the need to rotate the shaft or the collar.

Figure 5:
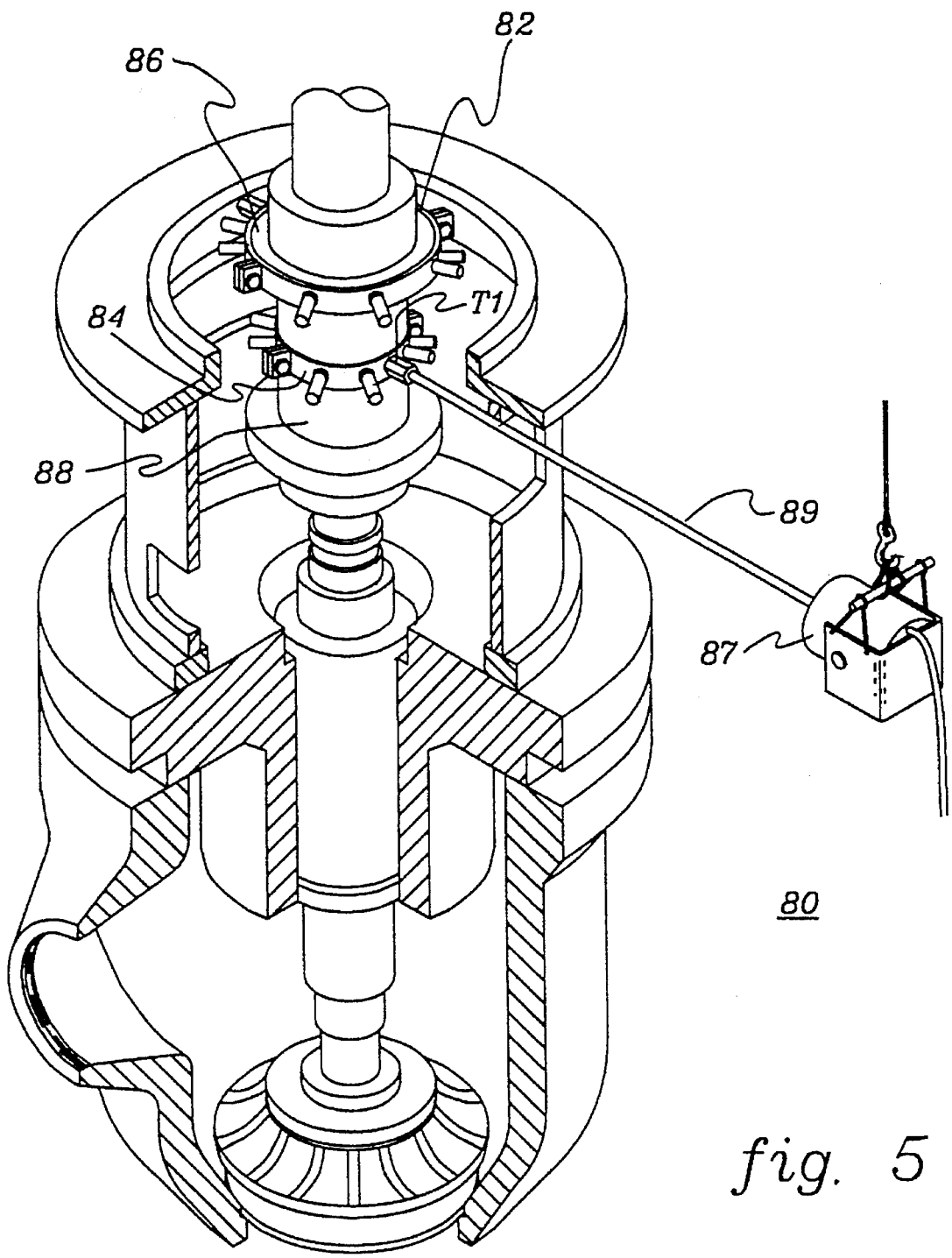
FIG. 5 is a partially broken away sectional view of an exemplary reactor coolant pump shaft test instrumentation arrangement for measuring radial vibrational response of the pump shaft utilizing collars of the subject invention according to a first approach.

FIG. 5 illustrates exemplary test equipment which can be used to measure the actual radial natural frequencies of the shaft system of reactor coolant pump 80. The shaft system is excited radially using an electromagnetic shaker 87 connected to the spool coupling 88 by a stinger 89 (i.e. a thin cylindrical rod). An input transducer T1 measures the input force and provides an electrical signal representative thereof. The vibration response of the shaft system is preferably measured simultaneously by multiple accelerometers mounted on spool collar 84 and hub collar 82 (see FIG. 6). The hub collar 82 is mounted to the upper coupling hub 86, which has a larger diameter than the coupling spool 88 to which the spool collar 84 is mounted. The output signals from hub collar 82 provide additional data for radial analysis, but a complete and accurate radial analysis can be performed using only the output data from spool collar 84. The output signals from the multiple accelerometers and input transducer are fed through a suitable coupler 91, as shown in FIG. 8, to a FFT analyzer 93 and optionally also to a digital tape recorder 95. The analyzer, in known fashion, provides a frequency response function, the peaks of which represent the actual natural frequencies. By exciting the shaft and measuring the system response simultaneously in multiple predefined radial directions around the shaft, one can observe the variation of the shaft system radial natural frequencies as a function of circumferential position. Also better correlation and higher reliability of the results may be achieved. Each peak in an FRF signifies a measured radial natural frequency.

Figure 6:
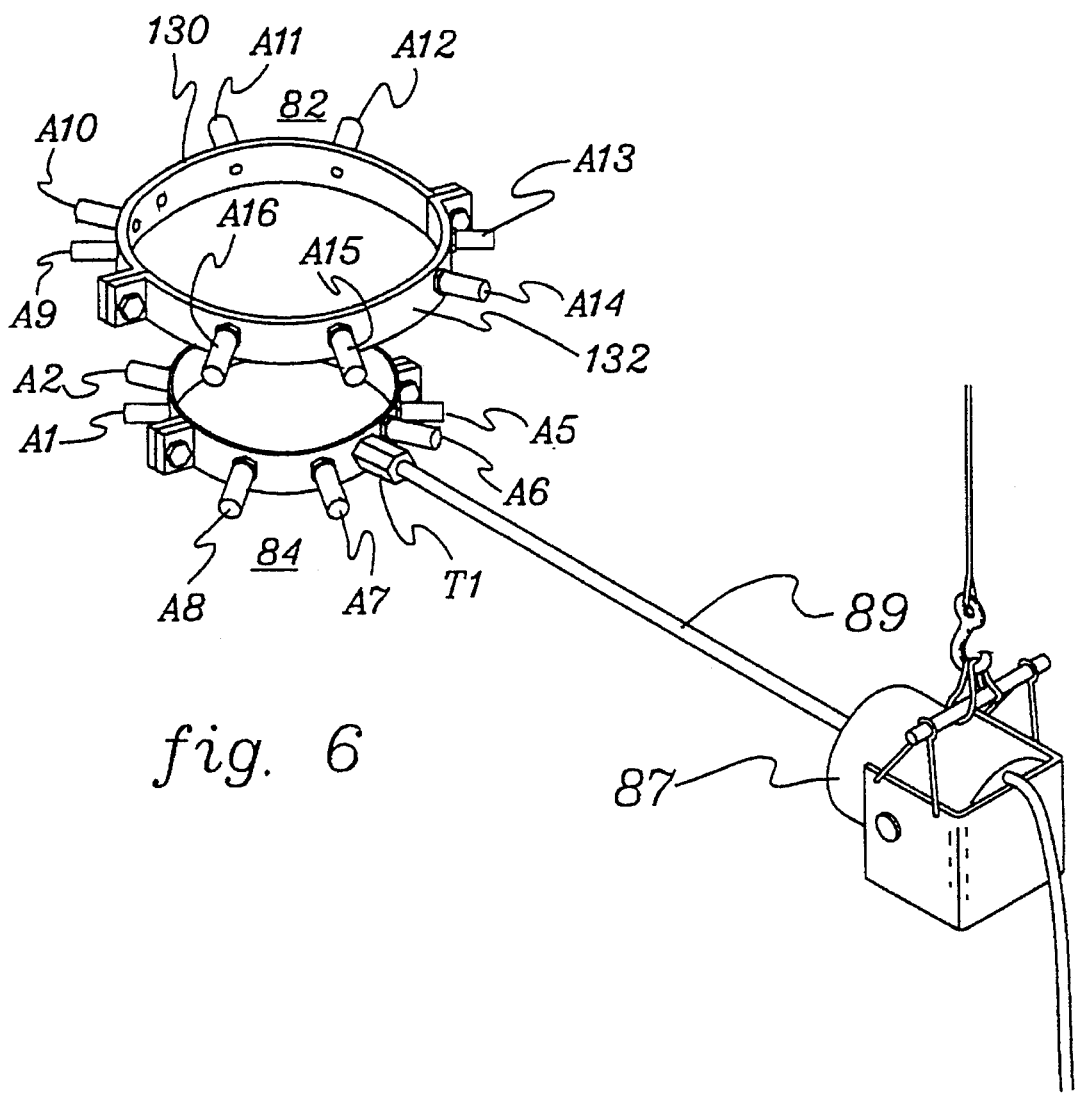
FIG. 6 is a perspective view of the reactor coolant pump shaft collars of FIG. 5.
Figure 7:
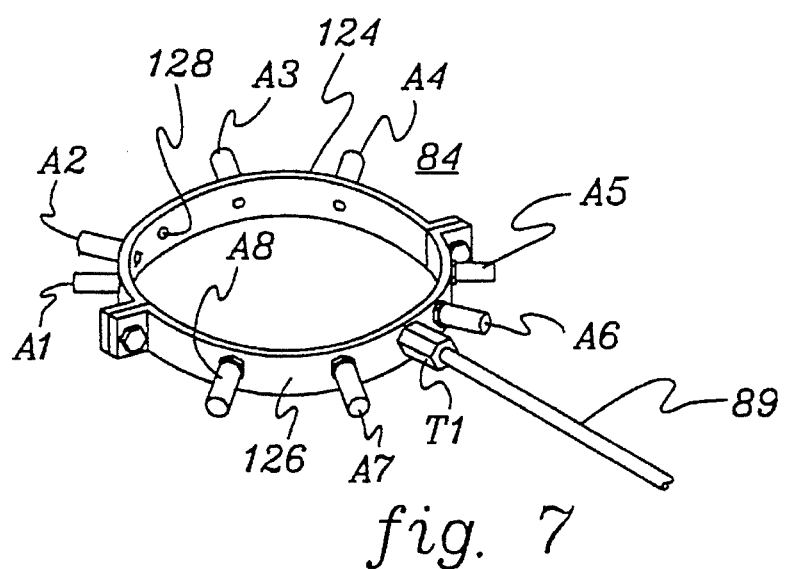
FIG. 7 is a perspective view of the reactor pump shaft spool collar of FIG. 6.

Perspective views of the hub collar 82 and the spool collar 84 are shown in more detail in FIGS. 6 and 7. The shaft (not shown) is excited radially using an electromagnetic shaker 87 connected to the spool collar 84 by a stinger 89, i.e. a thin cylindrical rod. An input transducer T1 measures the input force and provides an electrical signal representation thereof. The vibrational response of the shaft is preferably measured by multiple accelerometers A1, A2, A3, A4, A5, A6, A7 and A8 located at 45° intervals around the spool collar 84. The vibrational response of the shaft is also measured by multiple accelerometers A9, A10, A11, A12, A13, A14, A15 and A16 located at 45° intervals around the hub collar 82.

Spool collar 84 is illustrated in perspective view in FIG. 7. Two arcuate members 124 and 126 are connected (see FIB. 17 for connection of two arcuate members 202 and 204) so that the inner circumference of the collar fits snugly onto a pump shaft. One arcuate member 126 of the spool collar 84 has an input transducer T1 mounted thereon, with the stinger 89 attached thereto. Multiple output transducers A5, A6, A7 and A8 are also mounted on arcuate member 126. Two output transducer mounting holes are drilled at radial positions which are plus and minus 22.5° from the input force transducer hole. Two more output transducer mounting holes are drilled plus and minus 67.5° from the input force transducer hole.

The other spool collar arcuate member 124 is machined identically to the first arcuate member 126. The identical machining simplifies manufacturing of the collar, and results in a hole 128 in arcuate member 124. This hole corresponds to the input transducer mounting hole in which input transducer T1 of arcuate member 126 is mounted. Multiple output transducers A1, A2, A3 and A4 are mounted on the arcuate member 124. Two holes are drilled at radial positions which are plus and minus 22.5° from the hole 128. Two more holes are drilled plus and minus 67.5° from the hole 128. These are the output transducer mounting holes, and when the arcuate members 124 and 126 are connected, this places the multiple output transducers at 45° intervals from each other.

The hub collar 82 also has multiple output transducers A9, A10, A11, A12, A13, A14, A15 and A16 situated at 45° intervals from each other, with four located on arcuate member 130 and four located on arcuate member 132 (see FIG. 6).

Figure 8A:
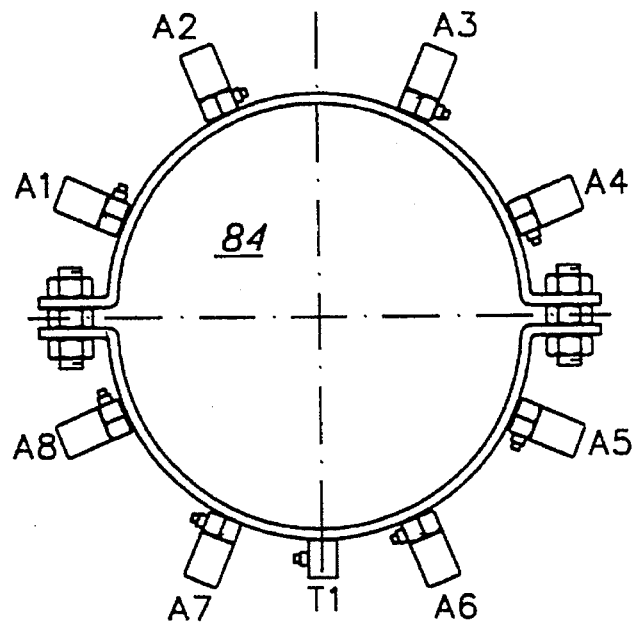
FIGS. 8A, 8B and 8C represent a radial test wiring scheme for the instrumentation arrangement shown in FIG. 5.
Figure 8B:
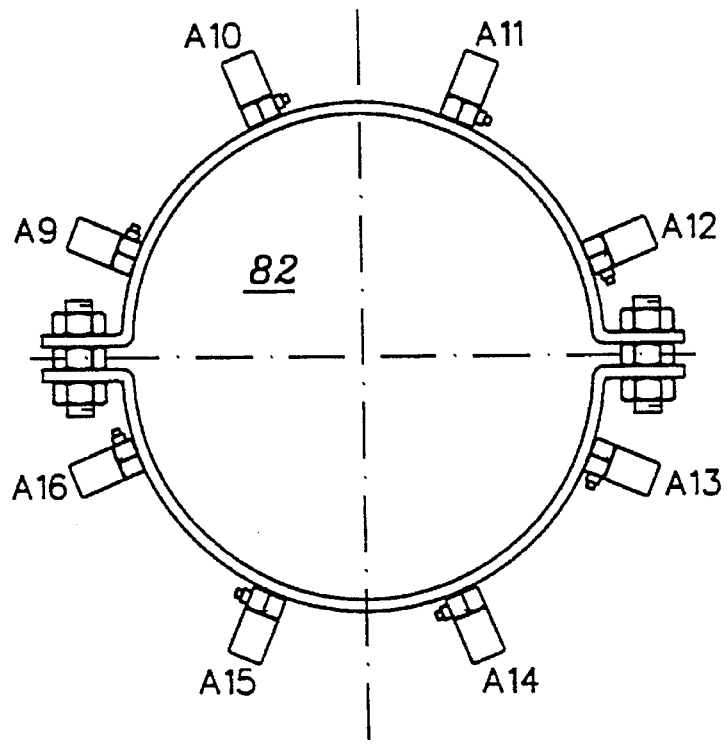
Figure 8C:
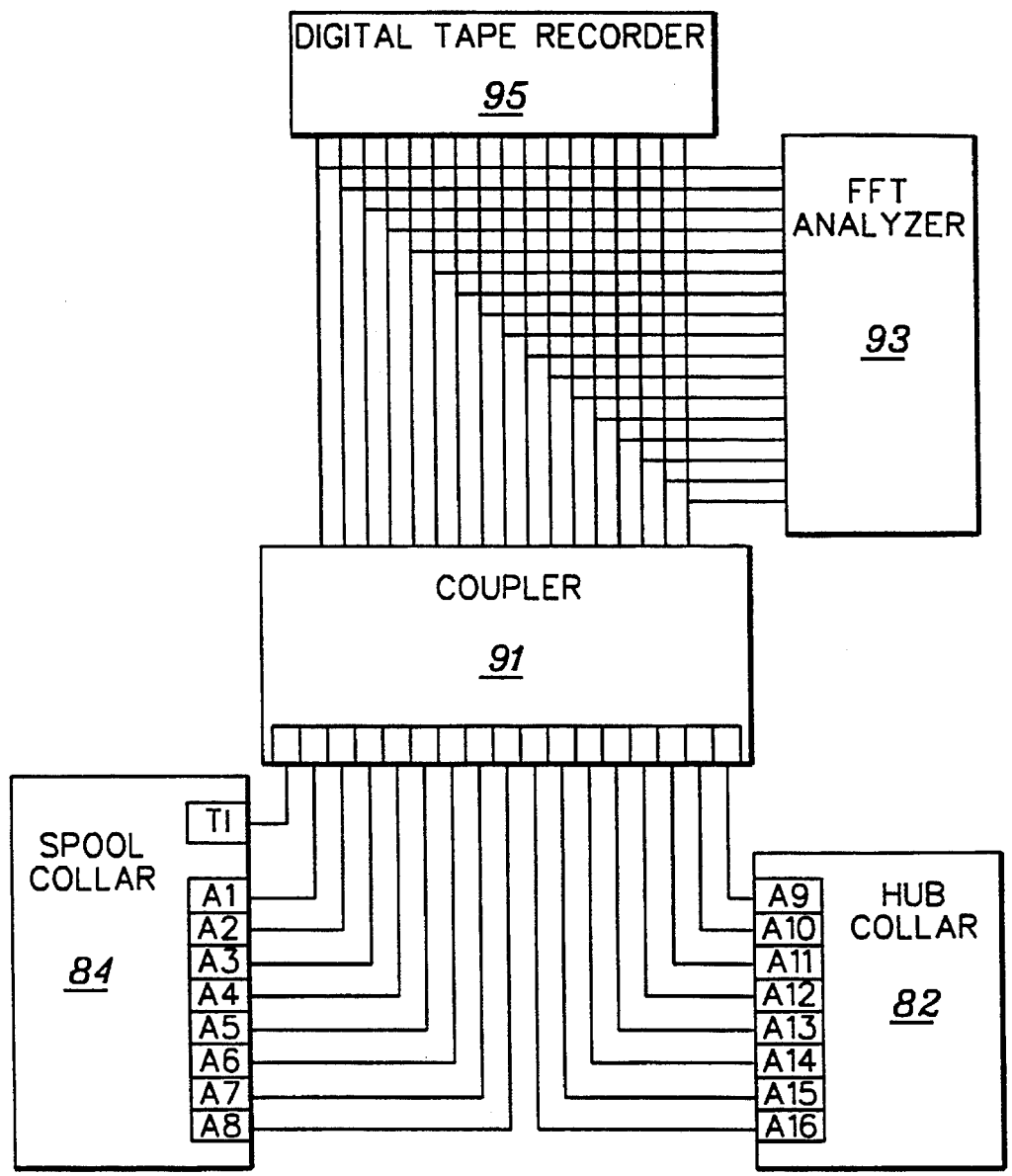

FIGS. 8A, 8B and 8C represent a radial test wiring scheme from the instrumentation arrangement shown in FIG. 5. The output signals from multiple accelerometers A1, A2, A3, A4, A5, A6, A7 and A8 on the spool collar, and accelerometers A9, A10, A11, A12, A13, A14, A15 and A16 on the hub collar, as well as from input transducer T1 on the spool collar, are fed through coupler 91 to a FFT analyzer 93 and a digital tape recorder 95. The FFT analyzer 93 provides the frequency response function, the peaks of which represent the actual natural frequencies.

Figure 9:
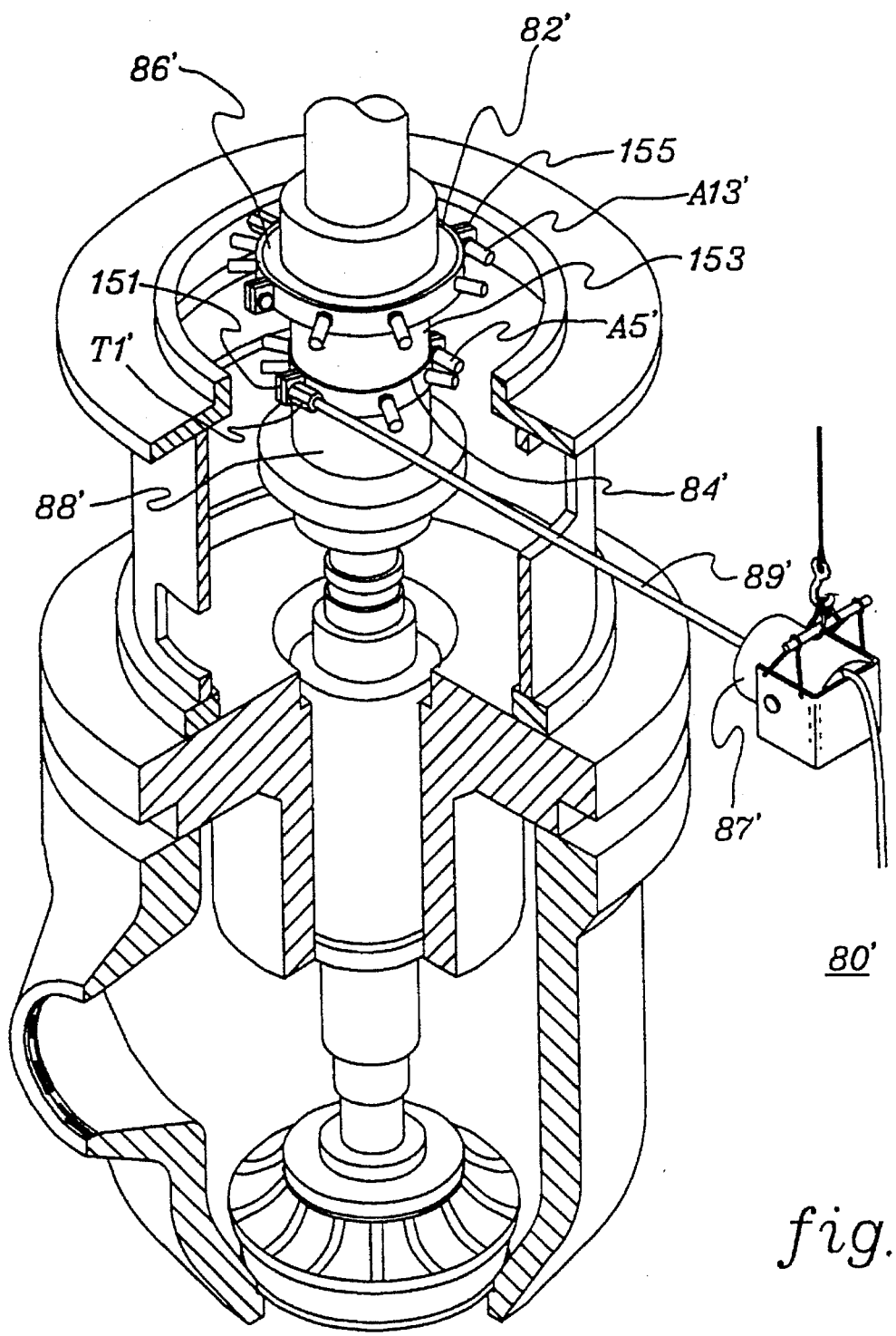
FIG. 9 is a partially broken away sectional view of exemplary reactor coolant pump shaft test instrumentation arrangement for measuring torsional vibrational response of the pump shaft utilizing collars of the subject invention according to a first approach.

FIG. 9 depicts an exemplary test instrumentation arrangement for torsional analysis using the collars previously shown from radial analysis. As shown, a tangential force excitation is applied using an electromagnetic shaker 87' through stinger 89' and torsional force input transducer T1' to a first set of tabs 151 on spool collar 84'. Torsional accelerometer A5' located on a diametrically opposed set of collar tabs 153 measures the torsional vibrational response of the shaft system about its polar axis. The torsional excitation is thus applied along a tangential direction at a first location on the circumference of spool coupling 88' and the torsional response is measured along a tangential direction at a second circumferential location displaced 180 degrees from the first location.

Torsional accelerometer A13' located on a diametrically opposed and axially displaced set of tabs 155 on hub collar 82' also measures the torsional vibrational response of the shaft system. In this case, the torsional excitation is applied along a tangential direction at a first location on the circumference of spool coupling 88' through spool collar 84' and the torsional response is measured along tangential direction at a second location displaced 180 degrees and axially displaced from the first location.

Signals from tangential input transducer T1' and torsional accelerometers A5' and A13' are processed in a fashion identical to that earlier described for radial analysis. In the torsional mode, only a single measurement reading, e.g. from torsional accelerometer A5' or A13' is required to determine an actual natural frequency for comparison with the modified model predicted shift of a natural frequency of interest as a function of crack ratio.

The arrangement of the collars 84' and 82' on reactor coolant pump 80' for the torsional test is shown in FIG. 9. The hub collar 82' is mounted to the upper coupling hub 86', which has a larger diameter than the coupling spool 88' to which the spool collar 84' is mounted.

Figure 10:
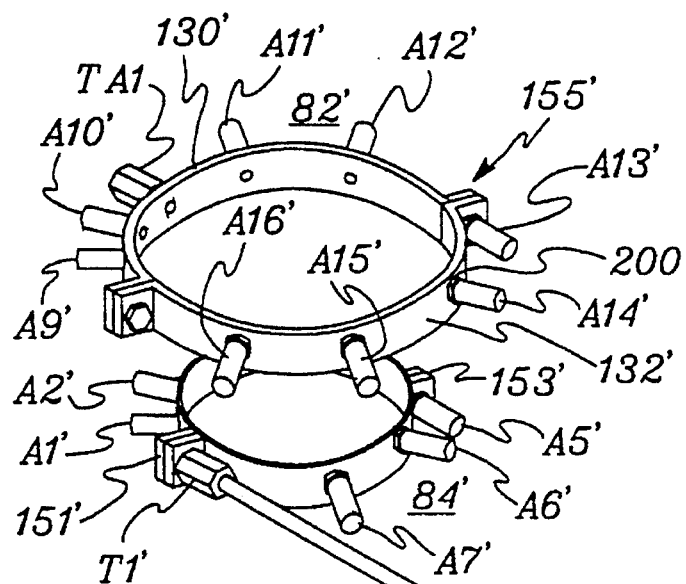
FIG. 10 is a perspective view of the reactor coolant pump shaft collars of FIG. 9.

A perspective view of the hub collar 82' and the spool collar 84' is shown in more detail in FIG. 10. The shaft (not shown) is excited tangentially using an electromagnetic shaker 87' connected to the spool collar 84' by a stinger 89' i e a thin cylindrical rod. A tangential input transducer T1' measures the input force and provides an electrical signal representation thereof. The torsional vibrational response of the shaft is preferably measured by multiple torsional accelerometers A5' and A13'.

Figure 11:
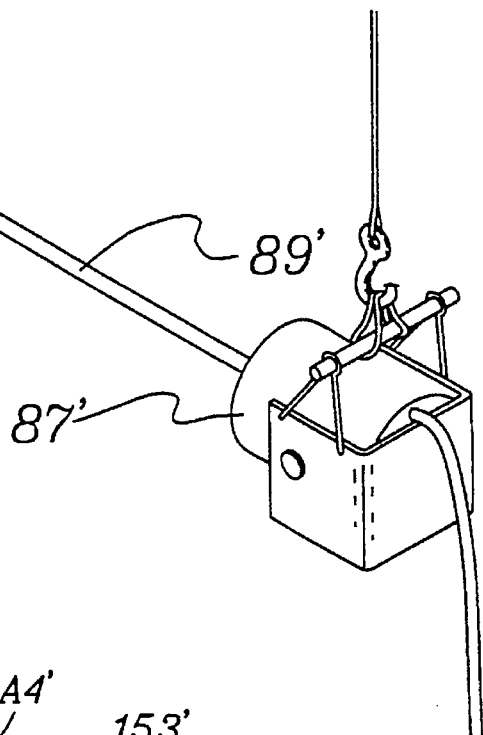
FIG. 11 is a perspective view of the reactor pump shaft spool collar of FIG. 10.
Figure 11:
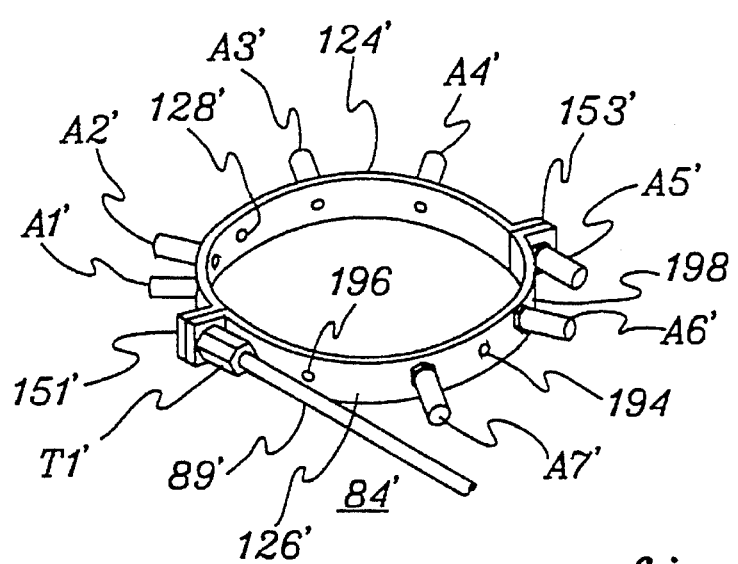
Figure 12A:
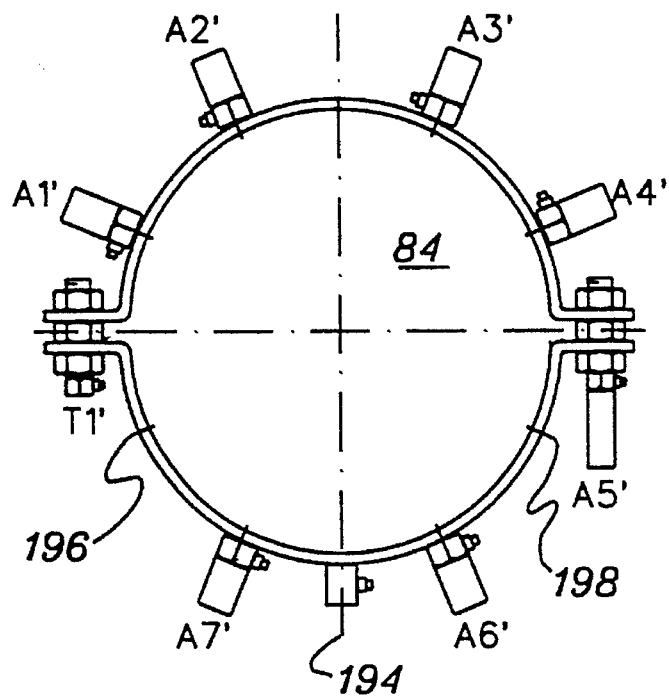
FIGS. 12A, 12B and 12C represent a torsional test wiring scheme for the instrumentation arrangement shown in FIG. 9.

Referring to FIG. 11, the input transducer Ti' with the stinger 89' attached thereto is mounted tangentially on spool collar 84' leaving hole 194 vacant, and output transducer A5' on spool collar 84' is shifted to be diametrically opposite the input transducer T1', leaving hole 198 vacant (see also FIG. 12A). Output transducer A8 on spool collar 84' is removed allowing positioning of the tangential input transducer T1' and leaving hole 196 vacant (see also FIG. 12A). On the hub collar 82', output accelerometer A13' is shifted to be diametrically opposite and axially displaced from input transducer T1' leaving hole 200 vacant (see FIG. 12B). An additional output transducer TA1 can also be located on hub collar 82' (see FIG. 12B and discussion below).

Accurate radial analysis measurements can also be taken using the test instrumentation arrangement shown in FIG. 9, utilizing input transducer T1' and output accelerometers A1', A2', A3', A4', A6' and A7' on the spool collar 84', as well as output accelerometers A9', A10', A11', A12', A14', A15' and A16' on the hub collar 88'.

Figure 12B:
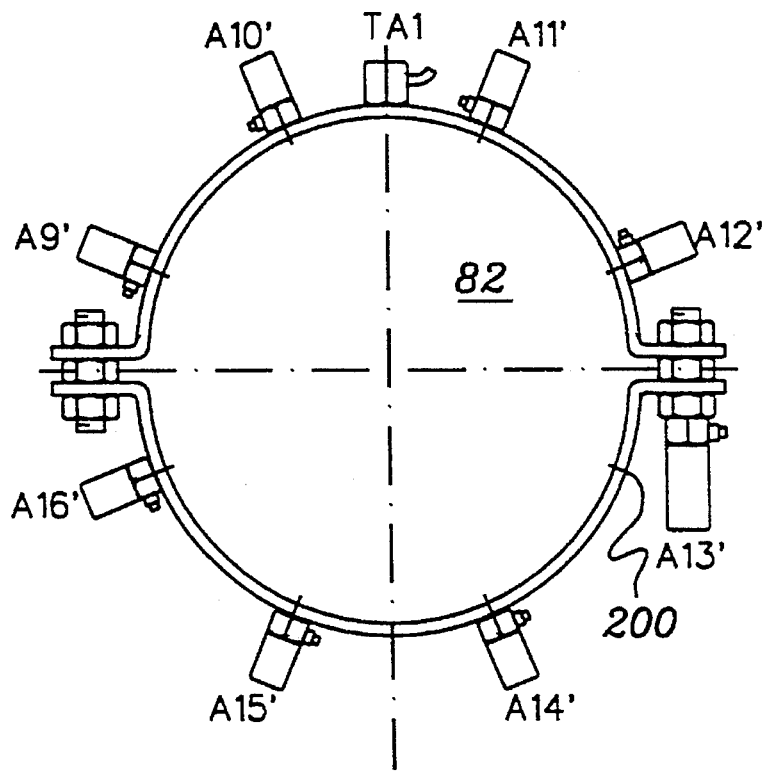
Figure 12C:
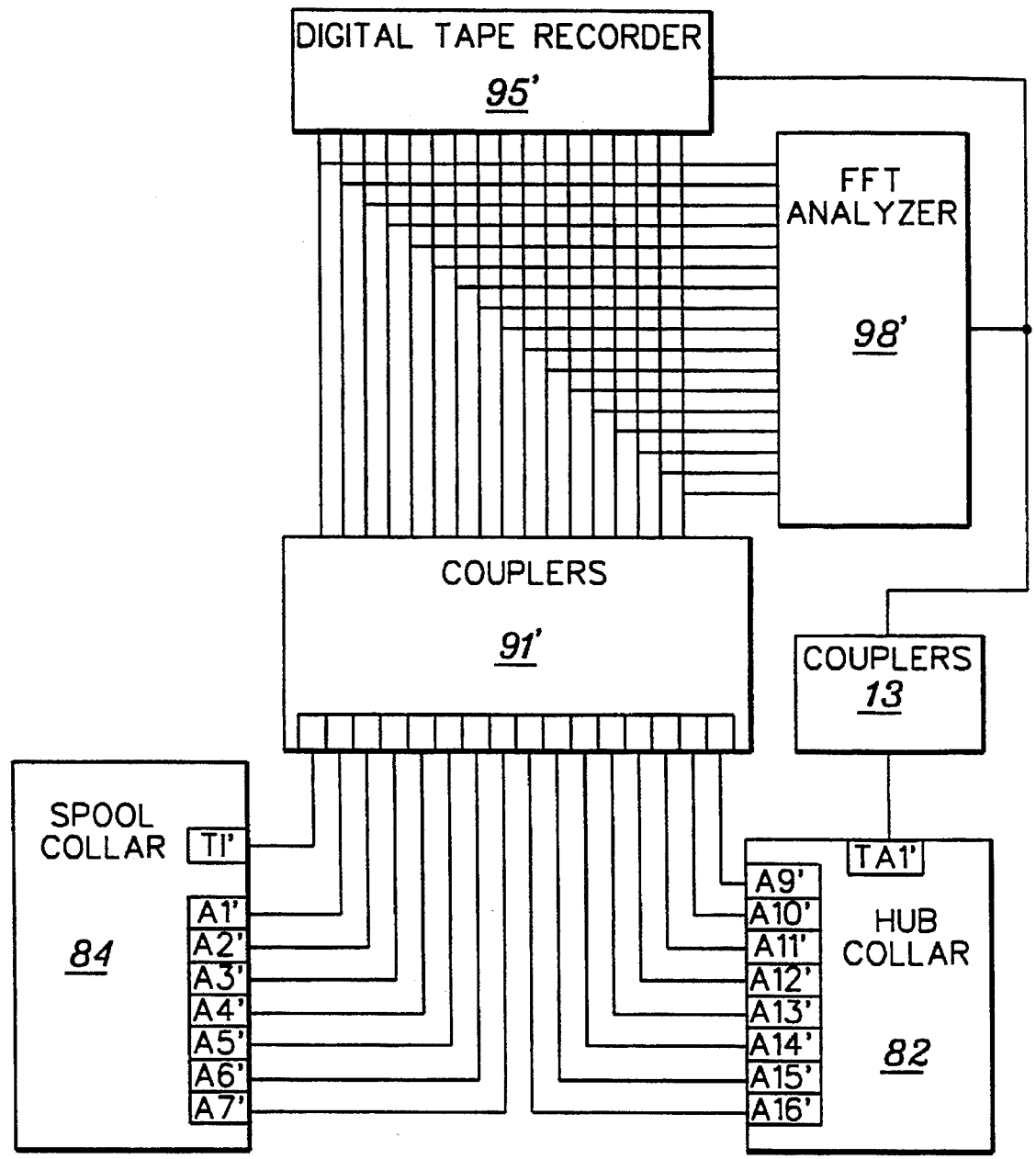

FIGS. 12A, 12B and 12C represent a torsional test wiring scheme for the instrumentation arrangement shown in FIG. 9. The output signals from multiple accelerometers A1', A2', A3', A4', A6' and A7' on the spool collar, and accelerometers A9', A10', A11', A12', A14', A15' and A16' on the hub collar, provide radial analysis data. The output signals from torsional accelerometers A5' on the spool collar and A13' on the hub collar, provide torsional analysis data. Additional data for torsional analysis is provided by the torsional accelerometer TA1 located on hub collar 82'. Output signals from input transducer T1' as well as the multiple output signals are fed through couplers 91' and 13 to a FFT analyzer 93' and a digital tape recorder 95'. The FFT analyzer 93 records the frequency response function, the peaks of which represent the actual natural frequencies.

As discussed above, a second collar is preferably utilized in the method, but is not required. It may be mounted to the upper coupling hub, which has a larger diameter than the coupling spool section. Alternatively, both collars may be mounted on the spool coupling, which is expected to improve data quality. The second collar is instrumented with the same output transducers as the first collar, but without input force transducers. The input energy from the spool collar is all that is required to excite the natural frequencies.

Data recorded from the second hub collar helps to correlate mode shapes with natural frequencies, since a given mode shape will have the same natural frequency at each of the test collars, but the phase information will vary. This phase information is compared to the mode shapes from the analytical model analysis. The radial test setup has an input force transducer and eight output transducers mounted on the spool collar, and an additional eight output transducers on the hub collar. The torsional test requires the removal of the two spool output transducers which are closest to the mounting bolts which connect the two arcuate members for sufficient clearance to mount the torsional input force transducer and the tangentially mounted output transducer to the spool collar. The output transducer closest to the mounting bolt on the hub collar is also moved to the bolt for the torsional test.

Data has been recorded from the radial output transducers during the torsional test with excellent results. Therefore, the method has been expanded to analyze the radial output transducer data recorded during the torsional test. Also, data has been successfully recorded from the torsional output transducers during the radial test.

The signals from the transducers are carried by cables to the test equipment. The cables are attached to a coupler. The coupler has two functions: first to send a constant current source to the transducers to power an integral voltage amplifier built into the transducers, and secondly to remove the dc voltage component from the data. These signals, which are raw time-based vibration data, are recorded on a digital tape recorder, while the frequency content of the data is monitored on a FFT (spectrum analyzer). The FFT has the capability to display the frequency response function. This is a frequency display of the output energy normalized by the input energy, thus identifying the natural frequencies of the test shaft. Also, the coherence of the frequency response function is monitored. The coherence value is an assurance of the quality of the data being recorded on the digital tape recorder.

Many channels may be simultaneously connected to the digital tape recorder and FFT. The number of channels recorded simultaneously depend only on the capability of the tape recorder. The method is valid with a minimum of only two channels recorded simultaneously. If the test engineer has only a two channel tape recorder, then the force input transducer would be recorded on channel 1, and the output transducers would be recorded, one at a time, on channel 2. If, however, the test engineer has an eight channel recorder, then the force input transducer would still reside on channel 1, but seven output transducers could be recorded simultaneously. Other alternatives could include a box to switch the various channels to the tape recorder and FFT.

Figure 13:
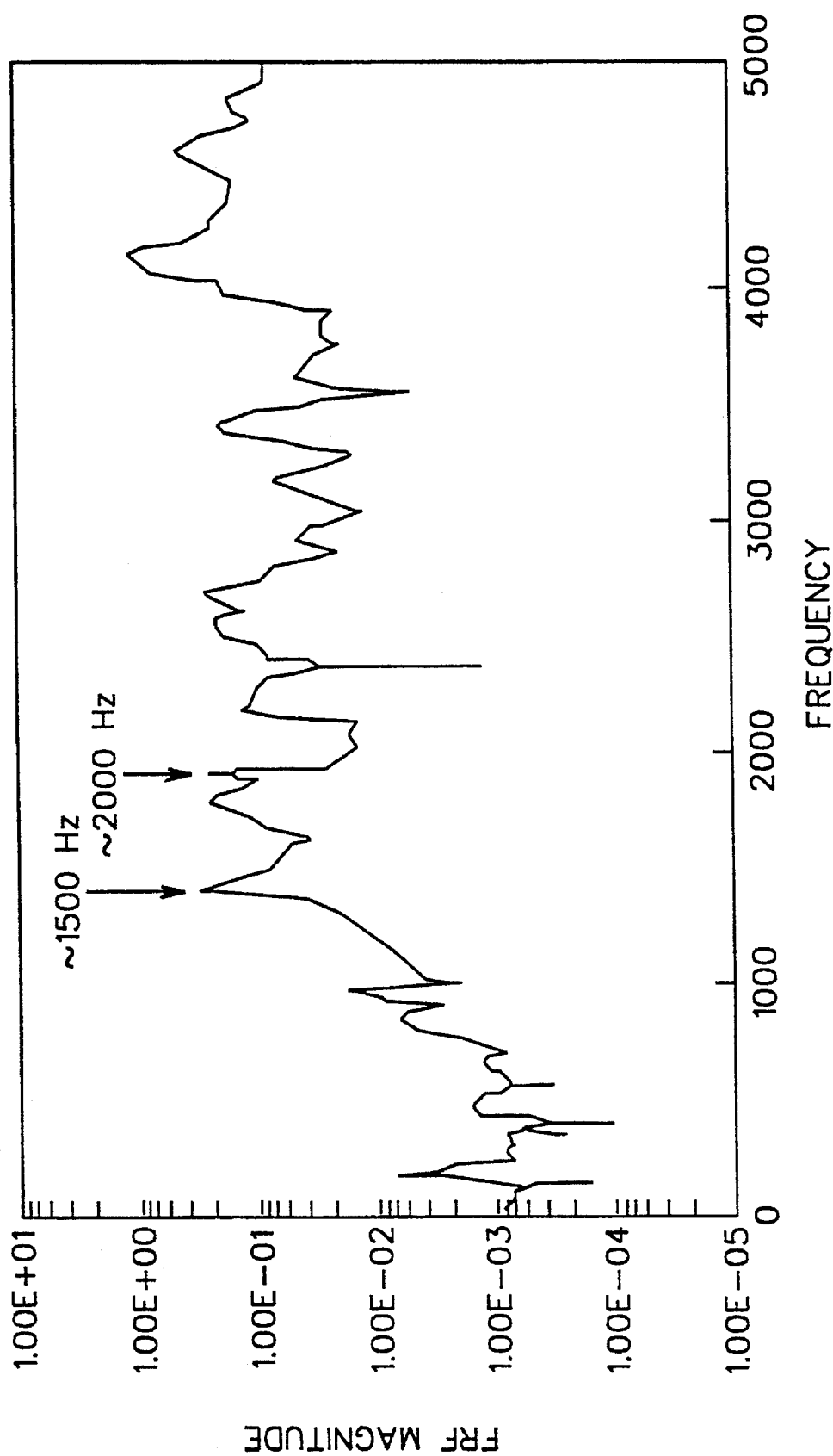
FIGS. 13, 14 and 15 are plots showing actual frequency response function measured simultaneously in accordance with the method of the present invention at three different output transducers numbered A3, A4 and A7, respectively.
Figure 14:
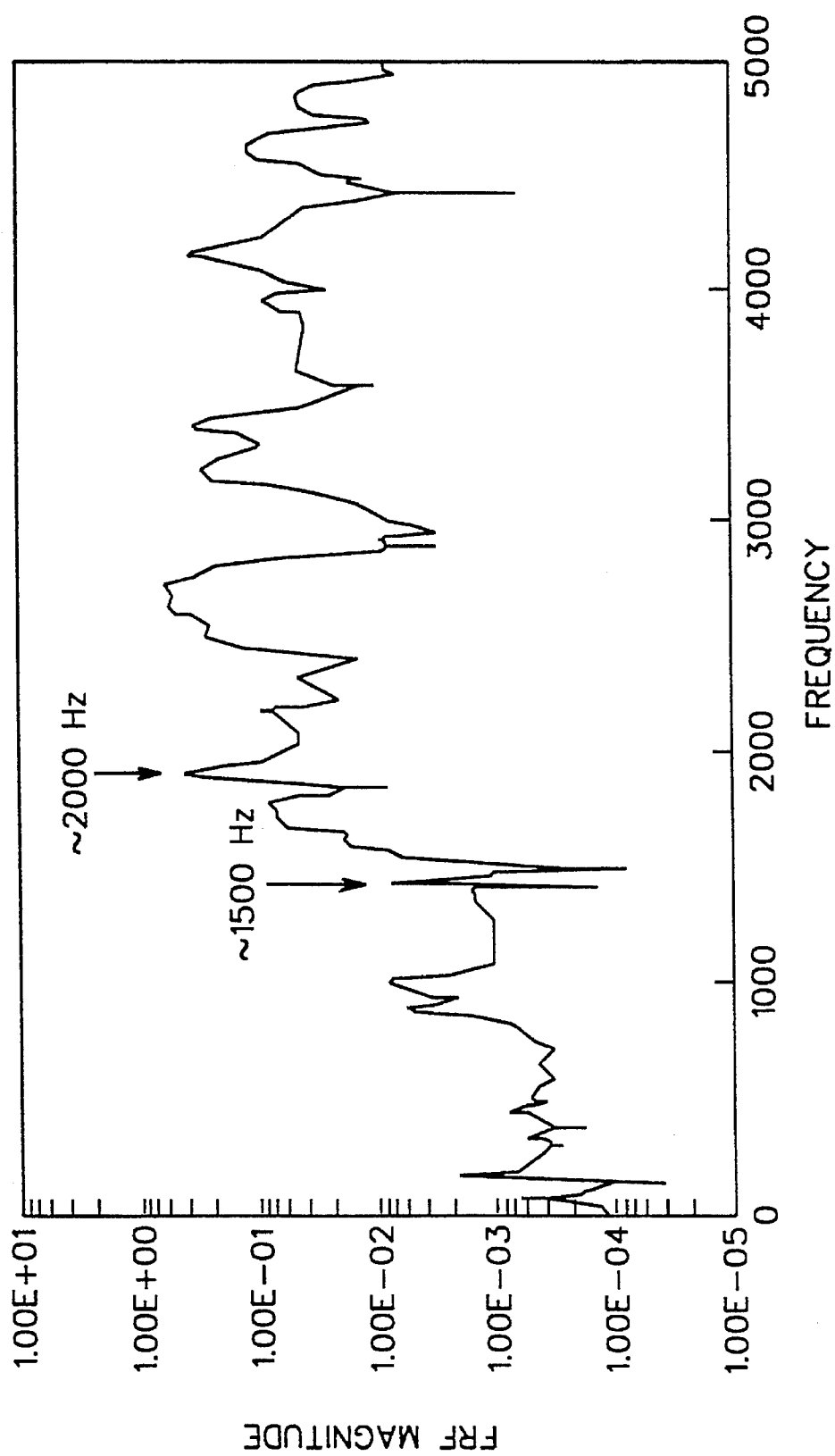

FIGS. 13 and 14 represent FRF's recorded on the spool collar during a radial test. Output transducer number A3 (output shown in FIG. 13) was approximately 200° from the input transducer, and number A4 (output shown in FIG. 14) was an additional 45° from number A3 or 245° from the input transducer.

Notice that a natural frequency at approximately 1500 Hertz is clearly identified by the number A3 transducer while the number A4 transducer data in the same region is questionable. It is questionable due to the sharp anti-resonances on either side of the peak. Transducer number A3 contains the true FRF which indicates there are no anti-resonances in the region. An anti-resonance is the technical name for a measurement point which exhibits zero vibration output for any amount of energy input. These are the points on the mode shape that are represented by nodes.

Another natural frequency is clearly identified by the number A4 transducer, while the same natural frequency is questionable on the number A3 transducer (just below 2000 Hertz). Thus, the simultaneous measurement of multiple output transducer readings allows better correlation and higher reliability of the results which are obtained.

Figure 15:
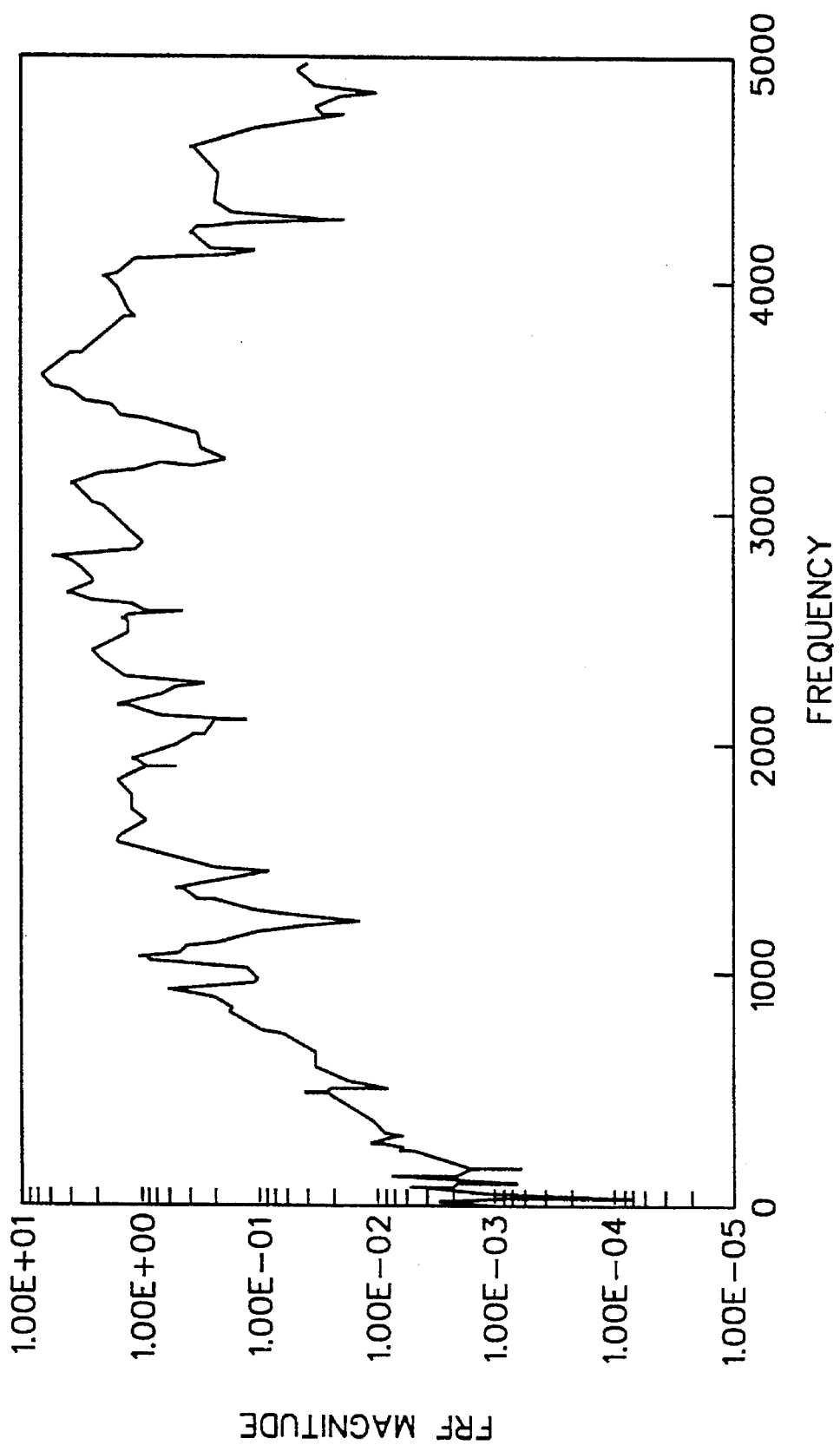

FIG. 15 represents an example FRF of a torsional input force and a radial output measurement at output transducer A7'. It has been recognized from experimental data that the torsional excitation provides an excellent means of exciting both torsional and radial modes, and that the measurement of these modes is again enhanced by recording several radial measurements for clear identification of both radial and torsional natural frequencies.

Figure 16A:
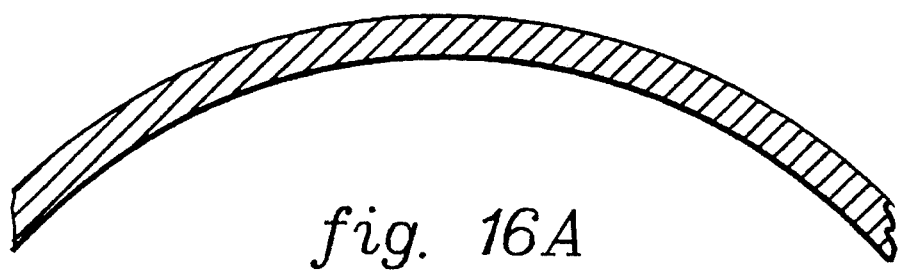
FIGS. 16A–D present a partial sectional view of the process of drilling, milling, and tapping of apertures in an exemplary collar of the subject invention for radial transducers according to a first approach.
Figure 16B:
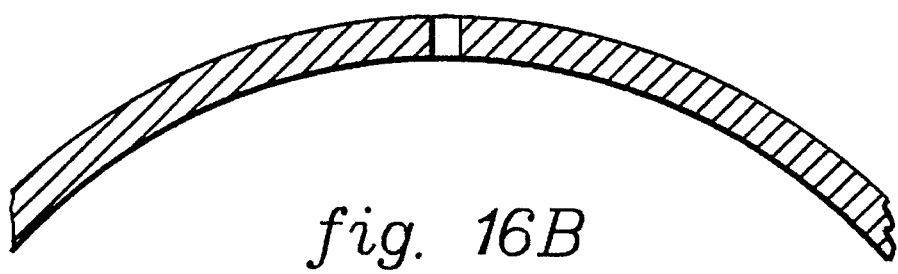
Figure 16C:
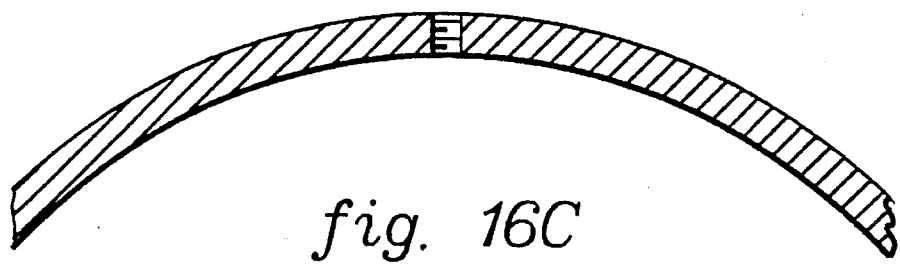
Figure 16D:
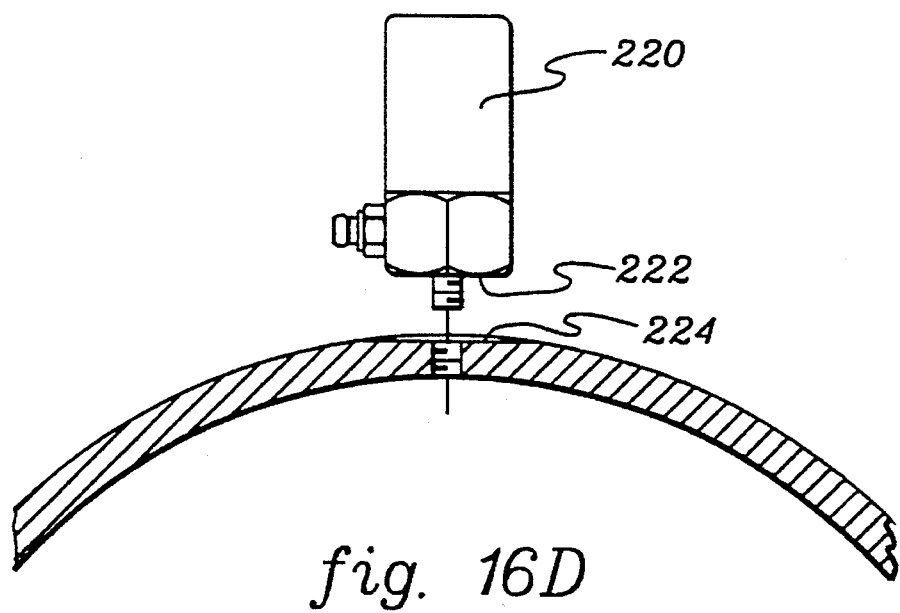

The collar may be fabricated from 1.5-inch-by-0.25-inch rectangular cold-rolled steel. This steel bar is rolled to approximate the curvature of the shaft diameter of the test item, as shown in FIG. 16A. Apertures in the steel for mounting input or output transducers are then drilled as shown in FIG. 16B, and tapped as shown in FIG. 16C. To ensure proper seating of the accelerometer 220 (or any input or output transducer), the steel is also milled (also called spot-facing) to create a flat 224 having a diameter slightly greater than the force transducer base 222 as shown in FIG. 16D.

Figure 17:
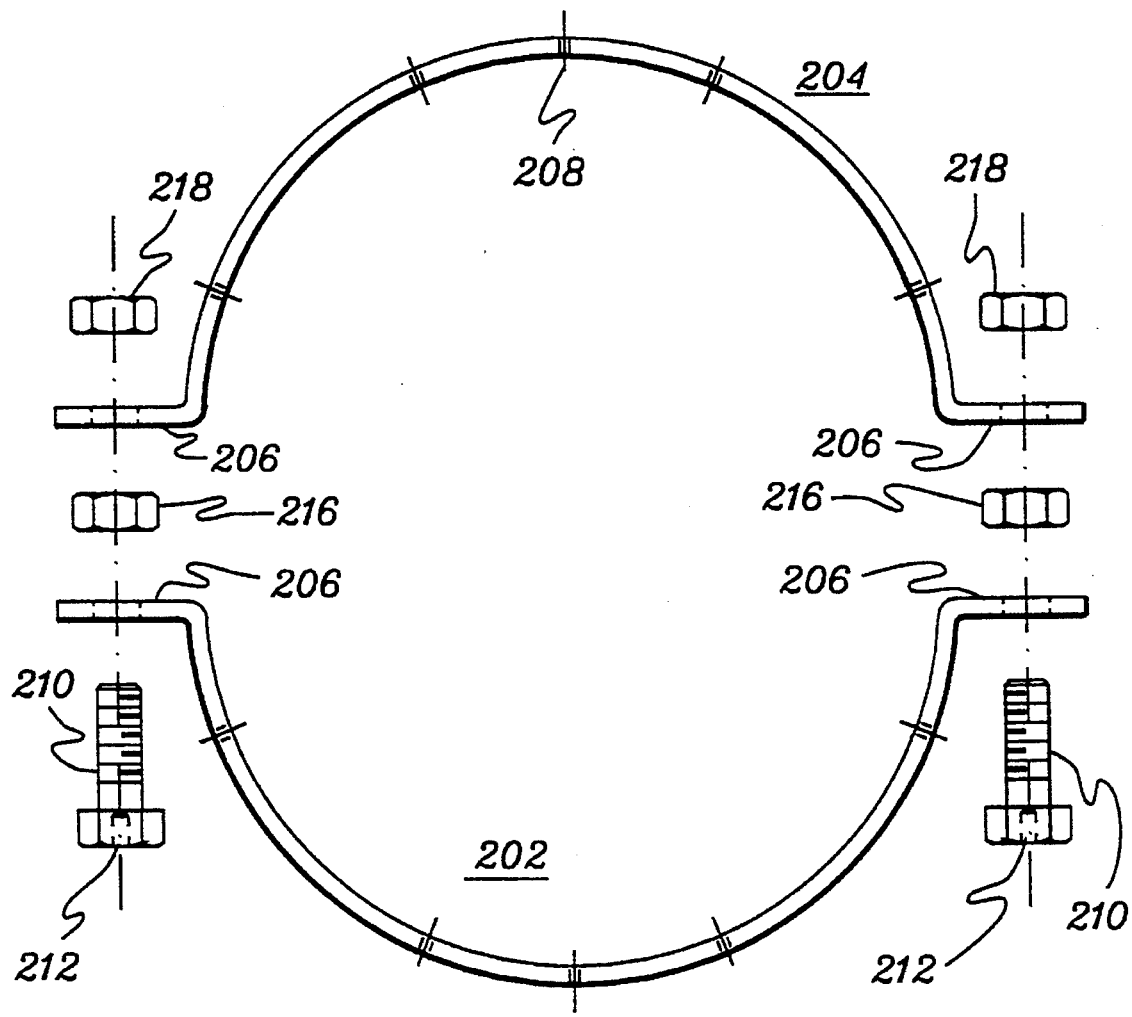
FIG. 17 is a top view of the collar of FIGS. 16A–D.

Referring to FIG. 17, two arcuate members are cut, such that each arcuate member 202,204 encompasses 180° of the shaft circumference. Tabs 206 are bent out at 90° at the end of each collar member 202,204 to provide a means for bolting the two arcuate members together about the shaft. The collar should fit snug to the shaft, and the bolts must be of sufficient stiffness to allow the collar to be tightened securely to the shaft. This is important for frequency content of the input and output energies.

Figure 18A:
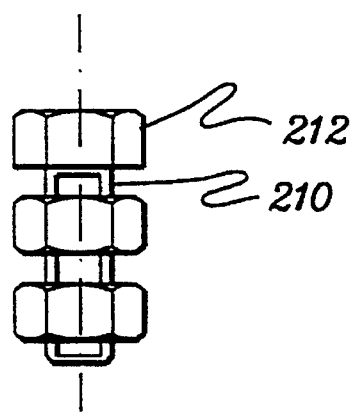
FIG. 18A, 18B and 18C are partially broken away side views of the drilled, milled and tapped bolt and nut arrangement shown in FIG. 17.
Figure 18B:
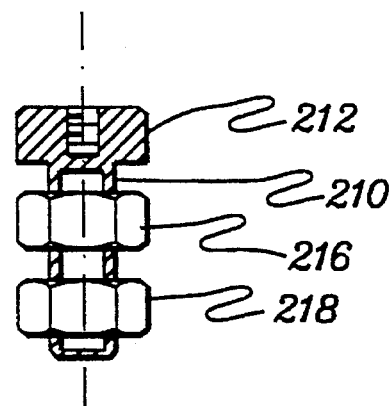
Figure 18C:
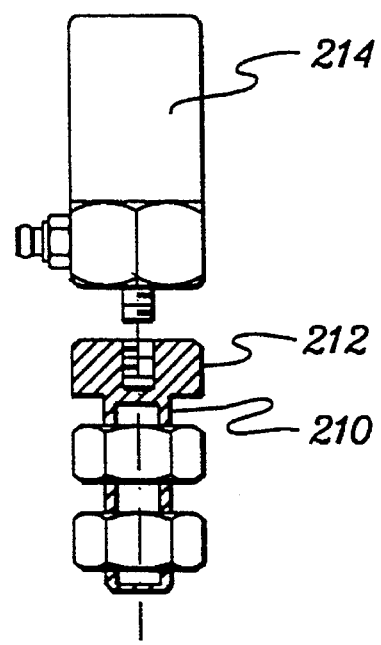

Referring also to FIG. 18, the bolts 210 which are used to clamp the two test collar arcuate members 202,204 to the shaft are hardened. The head 212 of each bolt 210 is drilled (FIG. 18B), tapped and milled (FIG. 18C) to accept the input force transducer 214 for the torsional excitation and the tangential output transducer. The bolts are securely fastened to one of the collar arcuate members. This reduces the amount of loose hardware that the test technician must handle. A jam nut 216 is used to attach the bolt 210 to the main collar member tab 206. Hex nuts 218 are used to tighten the second collar member 204 to the first collar member 202 firmly against the shaft, so that the collar cannot vibrate itself within a frequency range for which the shaft system is being tested.

Collars according to a second approach of the subject invention are now described in detail. Although these collars differ from those above in that they permit vibrational response measurements for multiple orthogonal axes at a common radial location on a single collar, they are used to detect shaft cracks in substantially the same way as the above collars. Some minor differences, however, between the use of the above collars and those by the second approach are discussed below.

Figure 19:
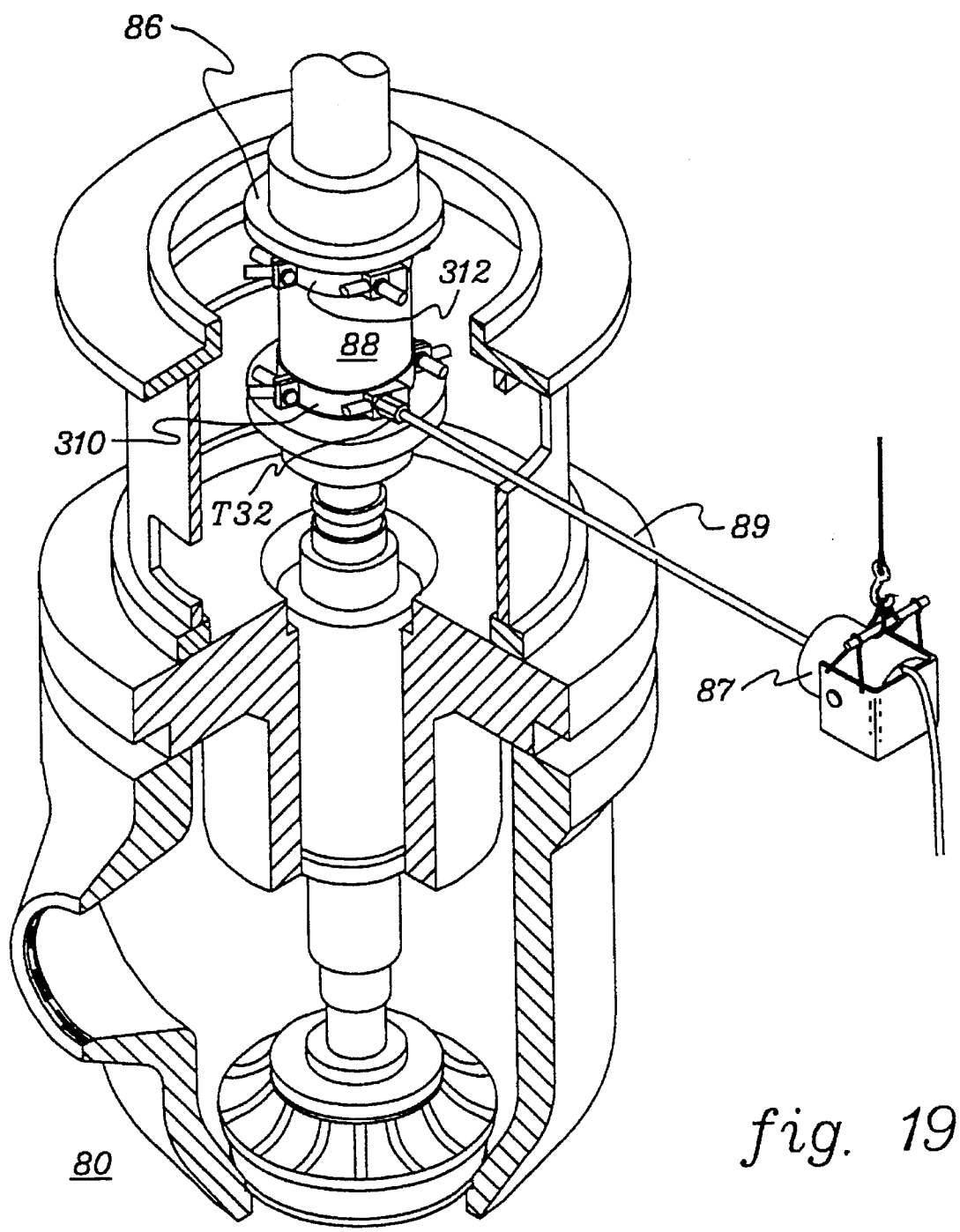
FIG. 19 is a partially broken away sectional view of an exemplary reactor coolant pump shaft test instrumentation arrangement for measuring radial vibrational response of the pump shaft utilizing collars of the subject invention according to a second approach.

FIG. 19 is a partially broken away sectional view of an exemplary test instrumentation arrangement for measuring the vibrational response of the shaft of reactor coolant pump 80 to a radial input force utilizing collars according to the second approach. The shaft system is excited radially using electromagnetic shaker 87 which is connected to the spool coupling 88 by stinger 89. An input transducer T32 measures the input force and provides an electrical signal representative thereof. The vibration response of the shaft system is preferably measured simultaneously by multiple accelerometers mounted on both a lower collar 310 and an upper collar 312. Lower and upper collars 310 and 312 are both preferably mounted on spool coupling 88. However, in other cases, lower collar 310 could be mounted above upper collar 312. Also, either lower or upper collar 310 or 312 could be mounted on one of the coupling hubs (e.g. upper coupling hub 86) as illustrated previously for the first approach. The output signals from upper collar 312 provide additional data for analysis, but a complete and accurate analysis can be performed using only the output data from lower collar 310. As for the first approach, the output signals from the multiple accelerometers and input transducer are fed through a suitable coupler to an FFT analyzer and optionally also to a digital tape recorder.

Figure 20:
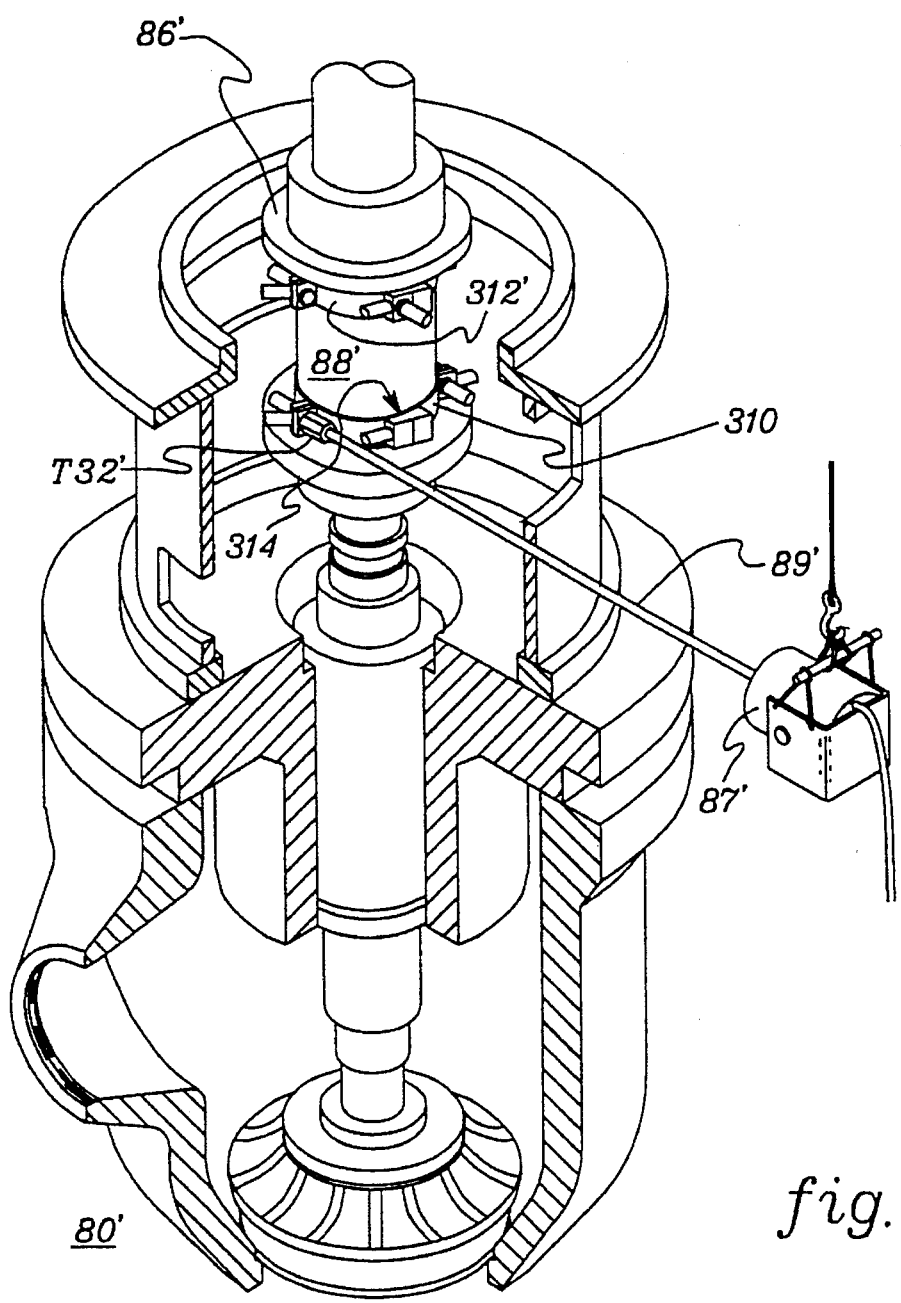
FIG. 20 is a partially broken away sectional view of exemplary reactor coolant pump shaft test instrumentation arrangement for measuring torsional vibrational response of the pump shaft utilizing collars of the subject invention according to a second approach.

FIG. 20 is a partially broken away sectional view of an exemplary test instrumentation arrangement for measuring the vibrational response of the shaft of reactor coolant pump 80' to a torsional input force utilizing the same collars as for the radial input test above. As shown, a tangential force excitation is applied using an electromagnetic shaker 87' through stinger 89' and torsional force input transducer T32'. The vibration response of the shaft system is measured simultaneously by the multiple accelerometers mounted on a lower collar 310' and an upper collar 312'. Collars 310' and 312' may be both mounted on spool coupling 88' and are preferably disposed in the same position as for the radial input test above to avoid the need to change position after performing the radial input test. However, in some cases these positions could be changed between tests, if desired, and one of the collars could even be mounted on upper coupling hub 86' or elsewhere. It should be noted that one radial output accelerometer has been intentionally removed from lower collar 310' (see point 314 in FIG. 20) to simplify sequential radial input and torsional input testing on the same pump shaft.

Figure 21A:
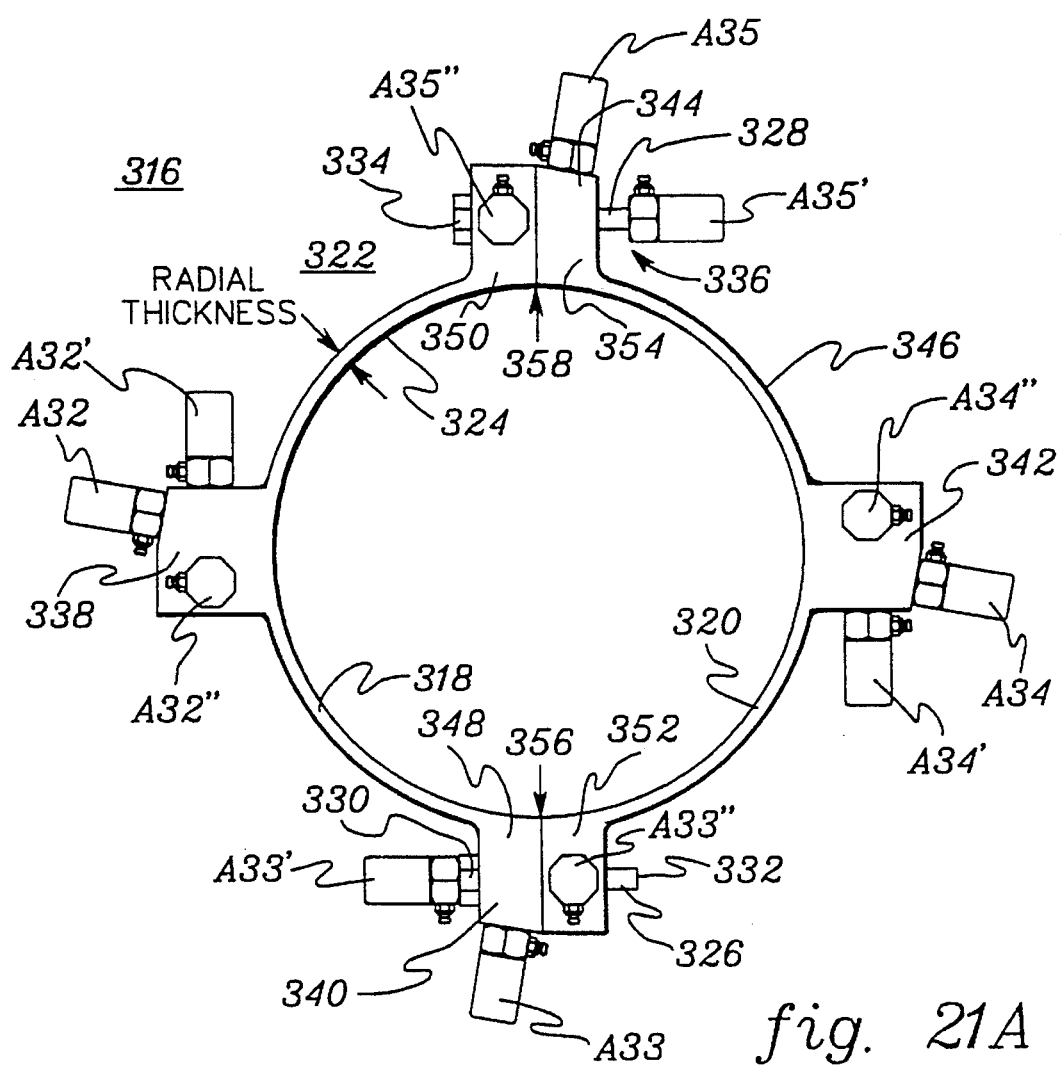
FIGS. 21A and 21B are top and side views, respectively, of a collar according to a second approach of the subject invention.
Figure 21B:
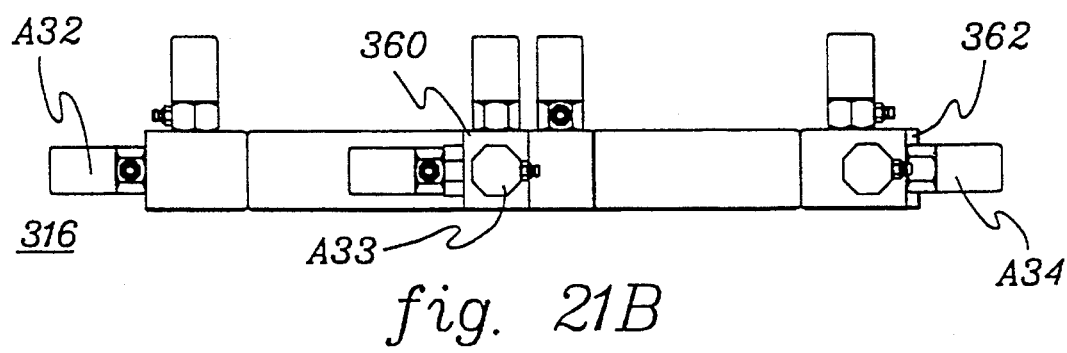

FIGS. 21A and 21B are top and side views, respectively, of a collar like those shown in FIGS. 19 and 20. In the preferred embodiment, all of the collars in FIGS. 19 and 20 have a substantially identical structure, but in other applications the structure could vary. For example, a collar of the first approach above could be used with a collar according to the second approach. Referring to FIG. 21A, a collar 316 has a first arcuate member 318 that is connected to a second arcuate member 320. Each arcuate member has a radial thickness 322, which is preferably substantially constant around the collar's circumference. The arcuate members are connected to form an inner collar circumference 324, which is sized so that the collar fits snugly onto a pump shaft. The first and second arcuate members are connected at their ends by connecting bolts 326 and 328. Both the head 330 and the threaded end 332 of connecting bolt 326 have apertures therein that are tapped and sized for mating with the stud of an accelerometer (see FIGS. 25A–25C). The head 334 and threaded end 336 of connecting bolt 328 have similar tapped apertures therein.

Four support blocks 338, 340, 342, and 344 are disposed around the outer collar circumference 346 of collar 316. Each of the blocks has five substantially planar faces with a sixth face adjoining the outer circumference of one of the arcuate members, and each block has a relatively large mass in comparison to that portion of the collar which supports it. Each of the blocks supports, for example, three accelerometers (e.g. block 338 supports accelerometers A32, A32', and A32"), which are oriented on each block in three substantially orthogonal directions (e.g. radial, tangential, and axial, all with respect to the major axis of the pump shaft being tested).

Blocks 338 and 342 are each formed from a single rectangular piece of metal. On the other hand, blocks 340 and 344 are formed by joining the ends of the first and second arcuate members. More specifically, first arcuate member 318 has two tabs 348 and 350, and second arcuate member 320 has two tabs 352 and 354. Tabs 348 and 352 together form block 340, and tabs 350 and 354 together form block 344. Blocks 340 and 344 are formed in this manner so that connecting bolts 326 and 328 can be torqued to a greater limit than for the collar by the first approach above. The larger, stiffer tabs of blocks 340 and 344 permit a higher bolting torque than is possible for the collar of the first approach and thus avoid undesirable deformation of the collar during torquing. Blocks 338 and 342 have a relatively large mass to correspond to that of blocks 340 and 344 so that the symmetry of the collar is maintained. Preferably, the connecting bolts are torqued to at least 40 N-m, and this higher torquing limit minimizes any relative motion between the shaft and the collar.

In measuring vibrational response, it is preferable that collar motion relative to the shaft be eliminated so that measurement noise is not generated by the output accelerometers. To help accomplish this goal, collar 316 is sized so that small gaps 356 and 358 exist after the connecting bolts have been fully torqued. These small gaps ensure that the snugness of the collar's fit to the shaft is determined by both the clearance between the outer circumference of the shaft and the inner collar circumference and the torquing limit of the connecting bolts. Otherwise, in the absence of gaps 356 and 358, tabs 348, 350, 352, and 354 may prematurely contact one another and prevent a fully snug fit by the collar to the shaft, even after full torque has been applied to the connecting bolts.

Another feature contributing to the stability of collar 316 is its rigidity. Collar 316 has a rigidity significantly greater than the collar of the first approach. The larger tabs of collar 316 (relative to those of the collar according to the first approach above) and the higher torquing limit of the connecting bolts substantially prevent vibrational noise caused by collar deformation and/or relative motion between the collar and the shaft. Eliminating this noise is advantageous because the objective is to measure the motion of the shaft itself. The accelerometers, however, measure only their own motion. To measure the true motion of the shaft requires that the accelerometers' motion and the shaft's motion be the same (i.e., that the relative motion between the accelerometer and the shaft be substantially eliminated within the frequency range being tested). Either relative motion of the collar with respect to the shaft or dynamic deformation of the collar (i.e. vibration) in the frequency range of the test would introduce noise and compromise data quality.

Collar 316 has multiple output accelerometers mounted thereon. Although, collar 316 is shown with only output transducers mounted, input transducers may be mounted as necessary to perform different types of tests, such as those shown in FIGS. 19 and 20. Radial accelerometers A32, A33, A34, and A35 are mounted so that their major axis intersects the center of the pump shaft, torsional accelerometers A32', A33', A34', and A35' are mounted so that their major axis is tangential to the outer collar circumference, and axial accelerometers A32", A33", A34", and A35" are mounted so that their major axis is parallel with the shaft's axis. Also, all accelerometers for a common measurement direction (e.g. radial, tangential, or axial) are disposed on the collar so that they are in phase. For example, the stud end of each torsional accelerometer is directed in the same positive cylindrical direction. Having the transducers oriented in phase is advantageous because it permits more direct comparison of the data from mulitple transducers. In the case of the torsional accelerometers, the in-phase configuration is accomplished, while maintaining collar symmetry, by mounting torsional accelerometers A33' and A35' in the ends of connecting bolts 326 and 328.

A significant advantage of collar 316 relative to the collar by the first approach above is its substantial symmetry with respect to both mass and stiffness. More specifically, collar 316 has support blocks and accelerometers disposed about its outer circumference so that substantial symmetry is maintained about a diameter drawn through the radial position of any of the support blocks. Such symmetry is beneficial because it prevents the introduction of asymmetrical effects into the measurement data. The technique for shaft crack detection for which this collar may be used is based on the detection of asymmetric stiffness in the shaft system due to a crack. An uncracked shaft will be symmetric in stiffness. The introduction of an asymmetric test collar might introduce indications of asymmetric stiffness into the data which could cause a misdiagnosis of the shaft's true condition. This may occur, for example, by false indications in the shaft data of the existence of a crack or of the true size of a crack.

Another advantage of the collar is the use of more than one torsional output transducer. Although vibrational response theory indicates that all tangentially-directed transducers should provide an identical output, this has been found not to be true. Instead, it has been learned that there are phase changes from one tangential location to another that are measurable with the collar according to the present invention. An additional advantage of the collar is that torsional accelerometers A32', A33', A34', and A35' are disposed at the same radial distance from the center of the shaft. This is due in part to the support blocks being of the same size and is advantageous because each torsional accelerometer will thus provide the same output signal amplitude for the same level of acceleration.

Referring to FIG. 21B, a side view of collar 316 is illustrated. The radial mounting faces of each support block (e.g. faces 360 and 362) are slightly oblique relative to a tangent of the outer collar circumference at the radial position of a respective support block. An example of one such tangent for accelerometer A33 would be a tangential vector with its origin at the radial position of gap 356 of support block 340. The radial accelerometers are obliquely mounted in this manner because blocks 340 and 344 are formed by joining tabs 348, 350, 352, and 354, and thus the mounting position of radial accelerometers A33 and A35 must be shifted away from gaps 356 and 358. Although this same problem is not present with radial accelerometers A32 and A34, in order to maintain symmetry throughout the collar, the mounting position of all radial accelerometers is shifted and the radial mounting face of each support block angled so that a center line drawn through the hole tapped into the face passes through the center of the shaft being tested and the equal angular spacing of the radial accelerometers about the collar is maintained.

Figure 22A:
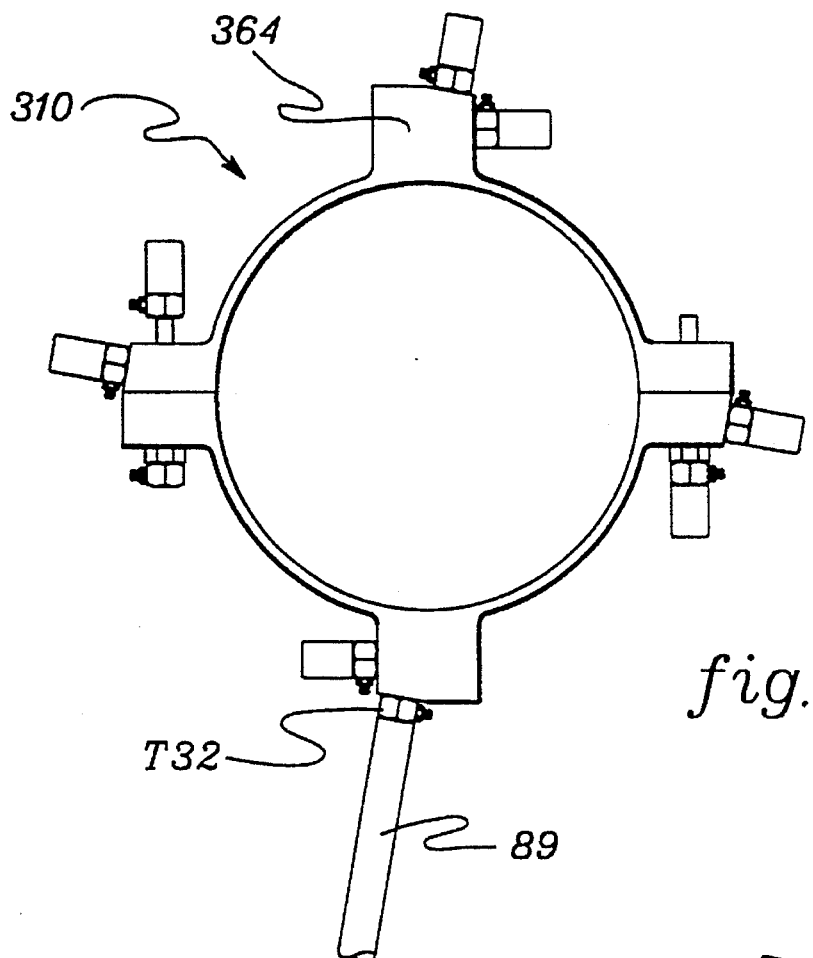
FIGS. 22A and 22B illustrate an input/output transducer configuration for the radial response test of FIG. 19.
Figure 22B:
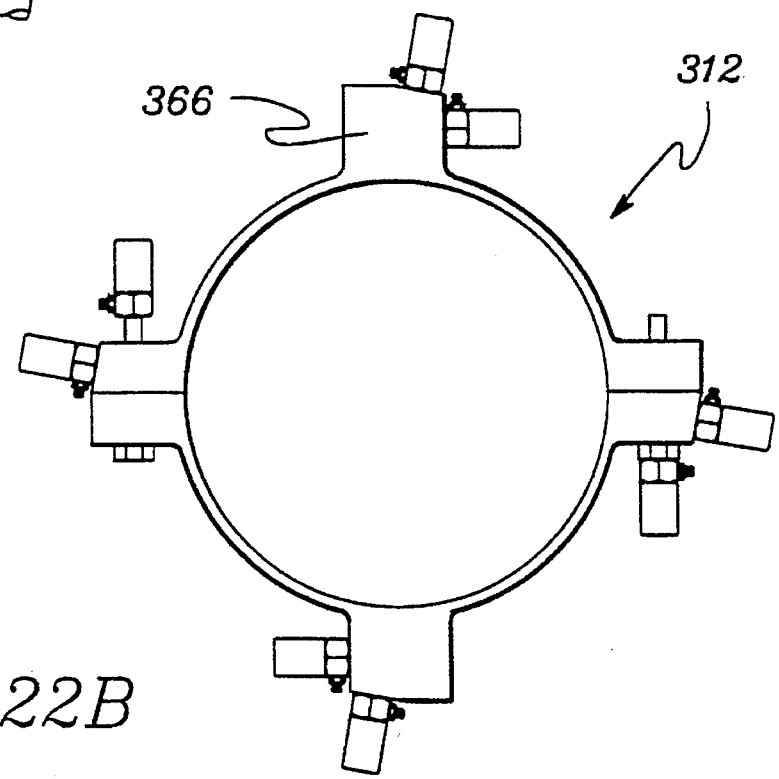
Figure 23A:
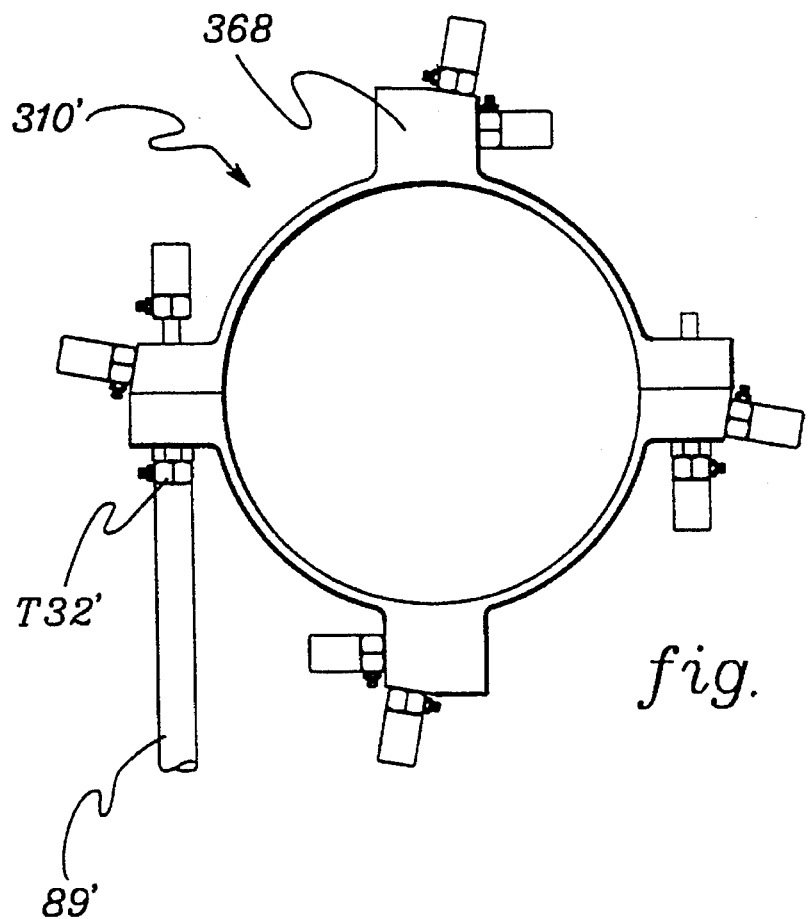
FIGS. 23A and 23B illustrate an input/output transducer configuration for the torsional response test of FIG. 20.
Figure 23B:
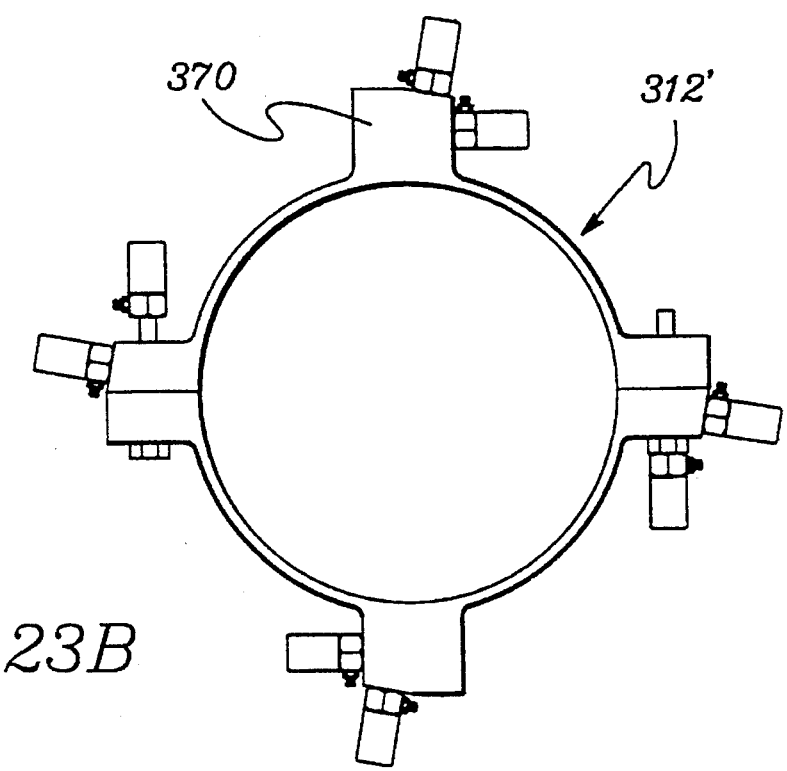

FIGS. 22A and 22B illustrate the input/output transducer configuration for the radial response test of FIG. 19 in greater detail. Collars 310 and 312 are shown in their preferred relative positions for testing. Preferably, lower collar 310 is in alignment with upper collar 312 on the shaft being tested such that, for example, support block 364 is positioned directly below 366, but this is not necessarily required. Similarly, FIGS. 23A and 23B illustrate the input/output transducer configuration for the torsional response test of FIG. 20. As for the radial input test of FIGS. 22A and 22B, it is preferable that lower collar 310' be aligned with upper collar 312' such that support block 368 is directly below block 370, but again this is not required.

Figure 24A:
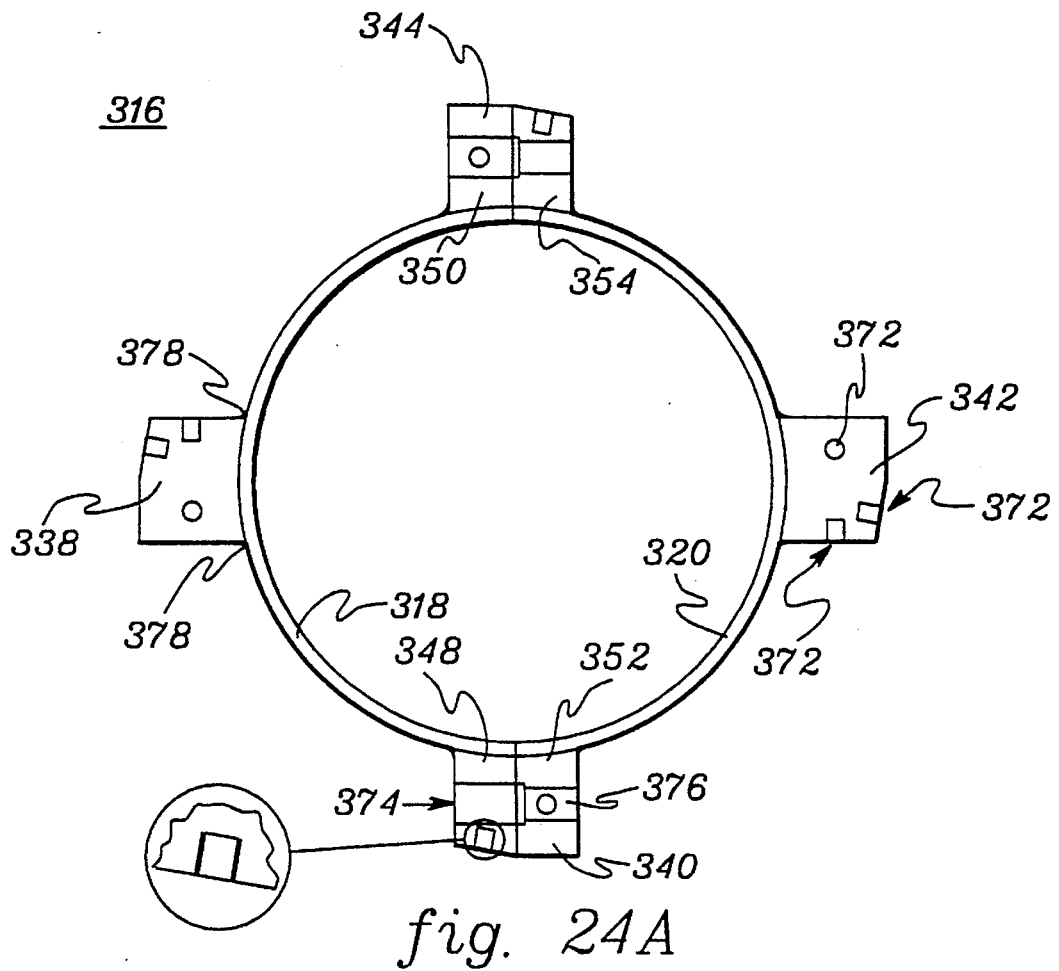
FIGS. 24A and 24B are partial sectional views of the collar of FIGS. 21A and 21B.
Figure 24B:
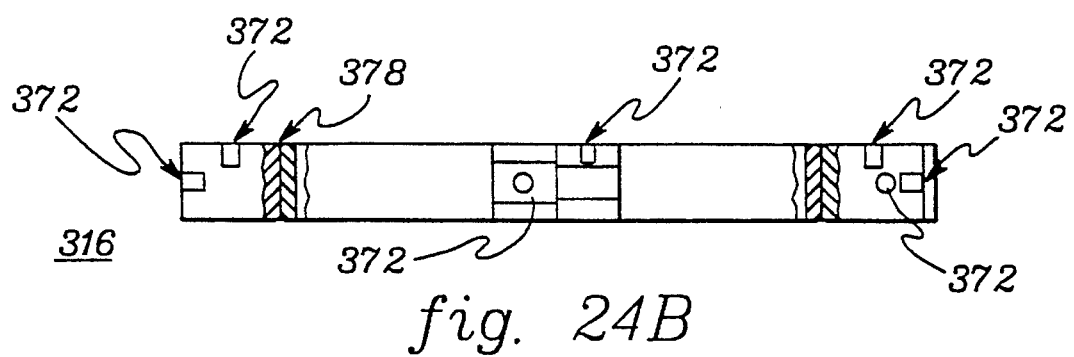

FIGS. 24A and 24B are partial sectional views of the collar of FIGS. 21A and 21B. FIG. 24A shows a partial cross-section of each support block 338, 340, 342, and 344. Each of these support blocks has apertures 372 drilled and tapped therein for mounting accelerometers. In addition, blocks 340 and 344 have apertures 374 sized for mating with connecting bolts 326 and 328. Apertures 374 have tapped ends 376 for mating with the threaded ends of the connecting bolts. The support blocks themselves are preferably attached to the collar either by welding or by cutting the entire collar assembly from a single plate using wire electric discharge machining (EDM). Each support block has two edges 378 which are machined to allow v-welds. Referring now to FIG. 24B, a side view of collar 316 is shown with a partial sectional view of the v-welds used at edges 378 and the disposition of apertures 372.

Figure 25A:
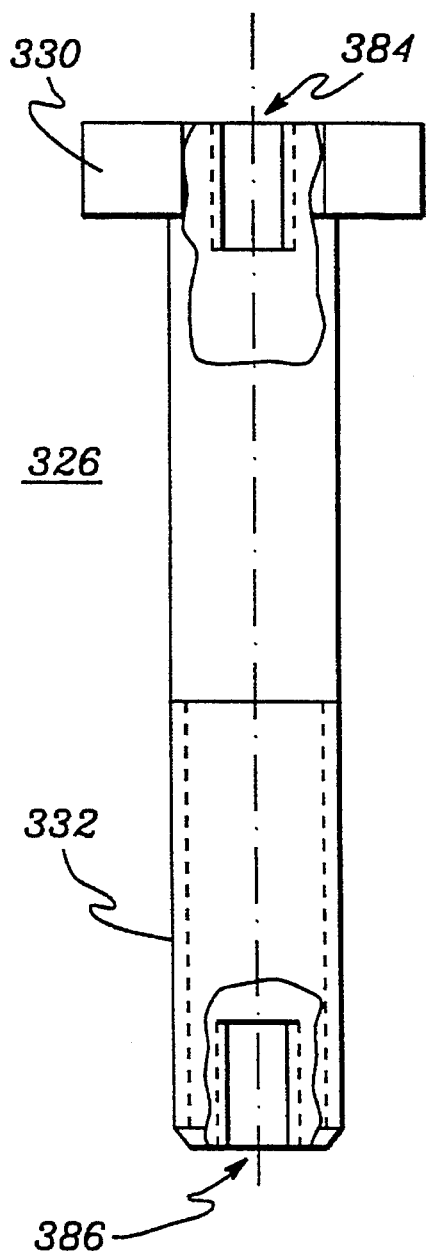
FIGS. 25A–25C are side, top, and bottom views, respectively, of a connecting bolt used in the collar of FIGS. 21A and 21B.
Figure 25B:
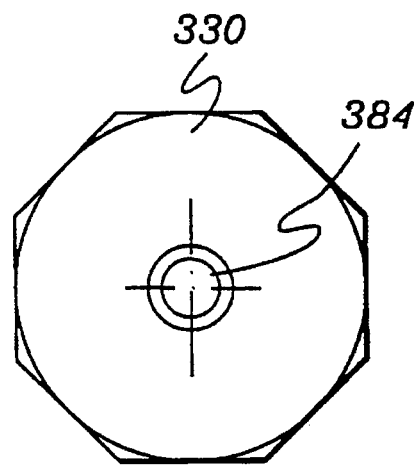
Figure 25C:
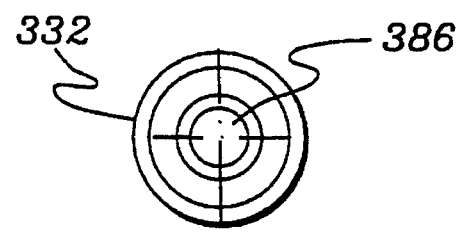

FIGS. 25A–25C are side, top, and bottom views, respectively, of connecting bolt 326 as shown in FIG. 21A. Head 330 of connecting bolt 326 has a tapped aperture 384 which is sized for mating with the stud of an accelerometer. Similarly, threaded end 332 has a tapped aperture 386 sized for mating with an accelerometer. The structure of connecting bolt 328 is preferably similar.

With respect to the formation of collar 316, it is preferably fabricated by cutting from a cold-rolled steel plate using wire electric discharge machining followed by the drilling and tapping of the various apertures as required. After fabrication, the collars are preferably sprayed with high-gloss enamel paint to aid in decontamination following use in a radioactive environment.

Figure 26A:
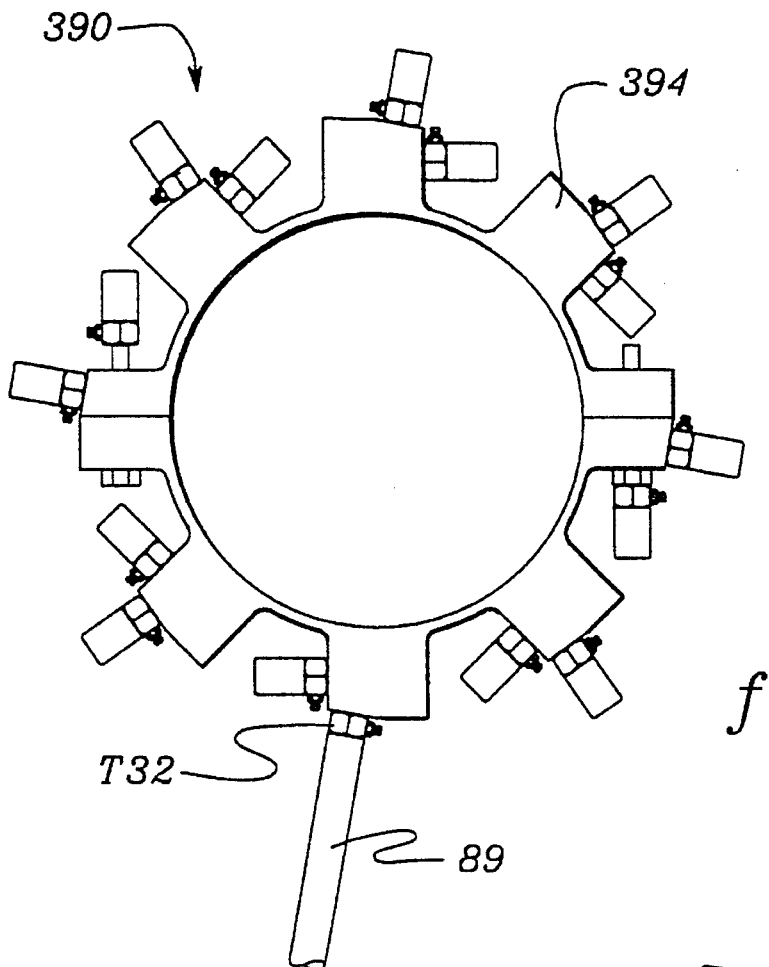
FIGS. 26A, 26B, 27A, and 27B illustrate input/output transducer configurations for radial and torsional response tests according to another embodiment of the second approach of the subject invention.
Figure 26B:
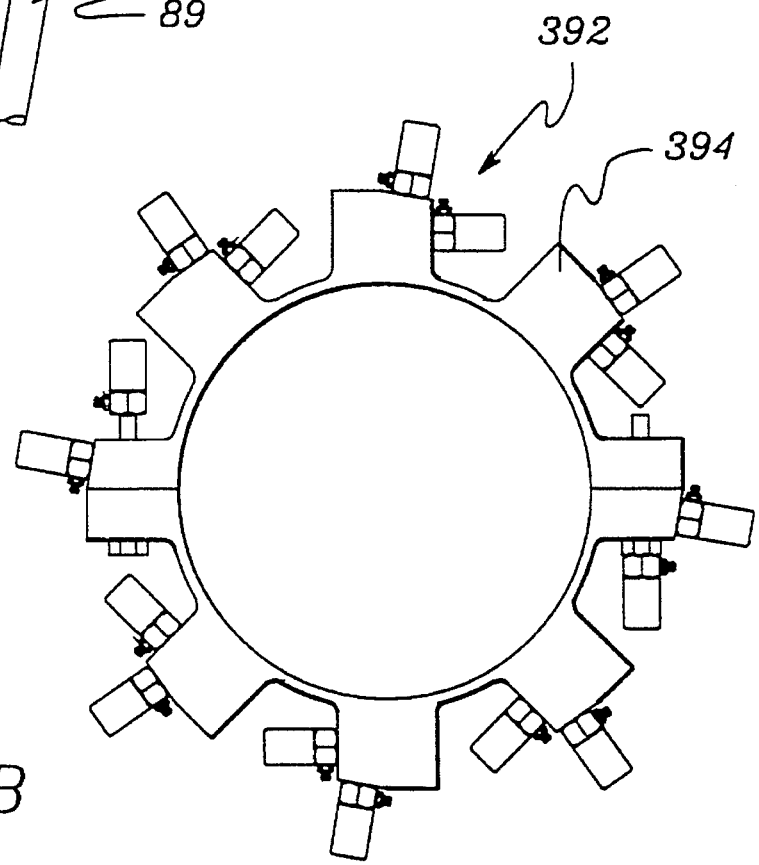
Figure 27A:
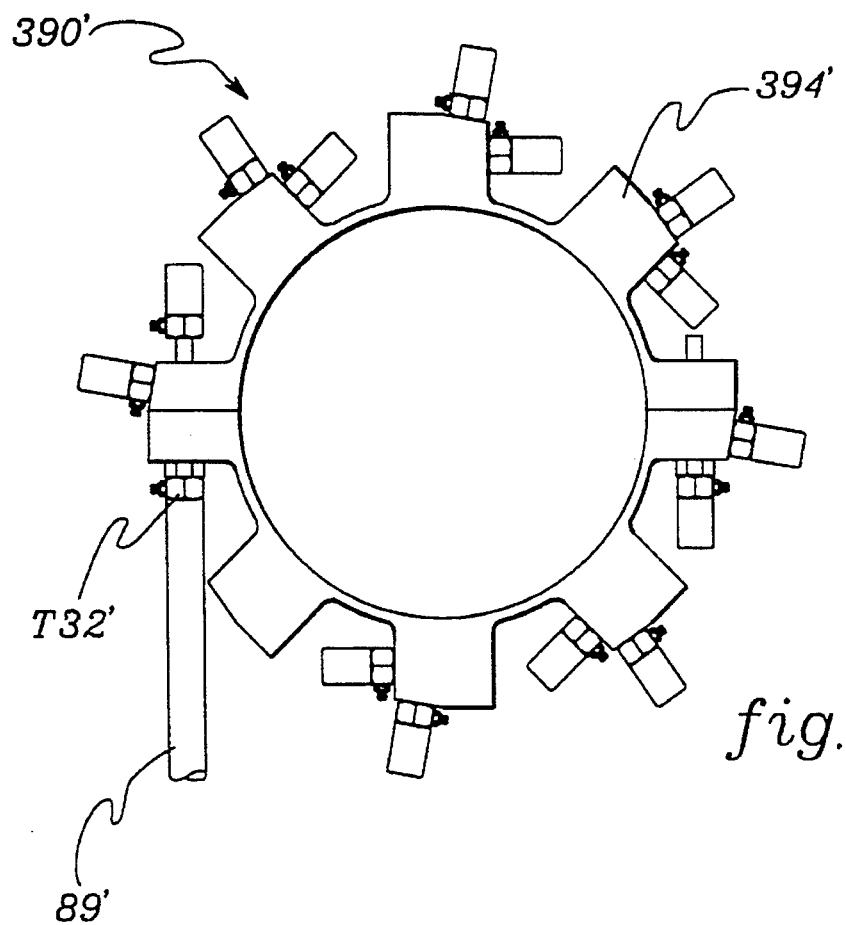
Figure 27B:
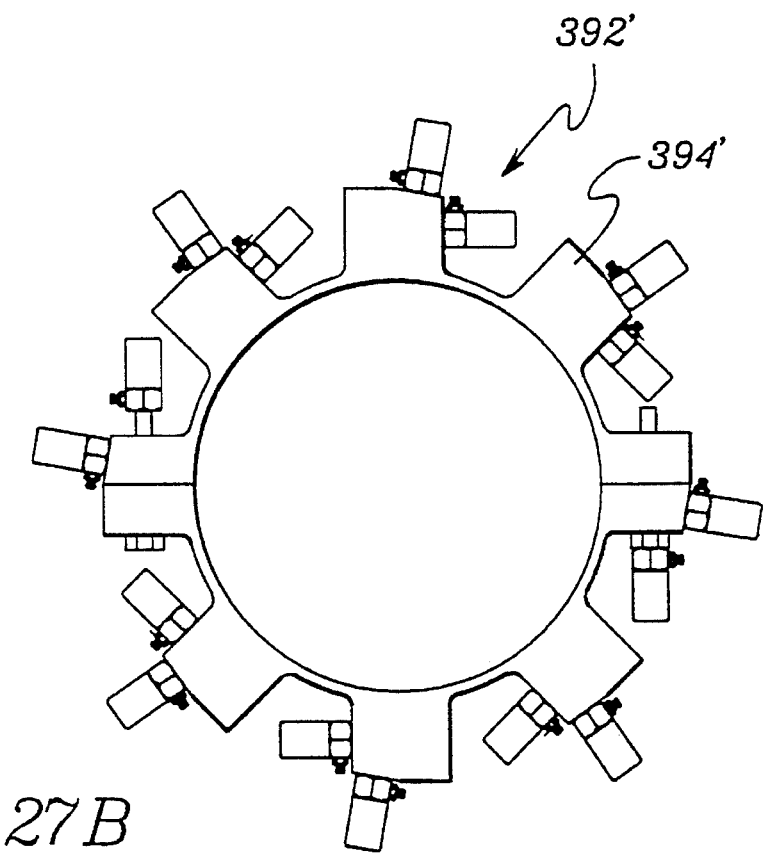

FIGS. 26A, 26B, 27A, and 27B illustrate input/output transducer configurations for radial and torsional response tests according to another embodiment of the second approach of the subject invention. Referring to FIGS. 26A and 26B, a lower collar 390 and an upper collar 392 each have eight support blocks 394, rather than four as for collar 316 above. The larger number of support blocks permits a greater number of output measurement channels during testing. Otherwise, however, the use of collars 390 and 392 is substantially similar to that of collar 316 described above. Referring now to FIGS. 27A and 27B, a lower collar 390' and an upper collar 392' also each have eight support blocks 394'. Again, their use is substantially similar to that described previously. It should be noted that collars 390, 392, 390', and 392' exhibit substantial symmetry with respect to mass and stiffness as does collar 316 above.

Another advantage of the collar according to the second approach is that the sensitivity, or other specification, of the accelerometers used for measurements in one direction may be chosen to be significantly different from that used for measurements in a second direction. For example, it is expected that the axial accelerometers will require a much greater sensitivity to provide meaningful output than either the radial or torsional accelerometers.

Various known equipment can be used to implement the instrumentation arrangements of the present invention. As an example, the following test equipment could be used to perform the cracked shaft modal testing.

1. A Hewlett-Packard HP3566A 16-channel Dynamic Signal Analyzer with an internal signal generator and an internal streaming disk is used as an FFT analyzer. The analyzer provides 16 channels of data acquisition capability with about a 12.5 kHz range and a resolution down to 65 micro-Hz. The internal disk permits the storage of time domain data for future zoom processing. An external DAT tape drive is preferably used for data backup. The internal ICP instrument support of the analyzer eliminates the need for external couplers 91 and 91' as previously used with the collars according to the first approach. The analyzer has a signal generator that provides for user selectable wave forms with either linear or logarithmic sweep rates. Sine, Triangle, or Square wave forms can be selected from 1 Hz to 12.5 kHz, and random noise is possible from DC to 12.5 kHz. Programmable bursting of any wave form is selectable including band limited white noise. The burst noise output provides decreased test time and reduced leakage errors. The analyzer is preferably run by a Toshiba T5200 portable computer, equipped with an HPIB instrument controller card, running HP data acquisition software (product numbers HP35634A and HP35637A) for the HP3566A under Microsoft Windows 3.1.

2. MB Dynamics Modal 50 Electromechanical Shaker with model 2250 Power Amplifier. The MB Dynamics Modal 50 Electromechanical Shaker has been especially designed for modal testing. The shaker can be easily suspended for quick alignment with the test piece. The power amplifier model 2250 amplifies the input excitation signal from the HP Signal Generator to drive the shaker. An inertial mass can be attached to the suspended shaker to react against the excitation force.

3. Kistler Instrument Corporation 1 Volt/G Accelerometer (0.5 to 5,000 Hz Range), 5516 Coupler; 9712 A50, 50 lb. force transducer, 99.2 mV/lb.; 5120 coupler with DC offset adjustment for use with the force transducer. The frequency limit of this accelerometer permits vibrational testing with the collars according to the subject invention up to 5,000 Hz, although it is expected that the collar may be used for testing at even higher frequencies with other transducers.

4. TEAC Model RD101T digital tape recorder. This recorder is optional (i.e. not required for testing).

The test method and instrumentation of the present invention can be applied to shafts having orientations other than vertical (e.g. horizontal) and to symmetrical structures other than rotors and rotatable shafts. A similar approach can be used to identify cracks in a horizontal turbine shaft having a central bore and other similar structures.

Although preferred embodiments have been depicted and described in detail herein, it will be apparent to those skilled in the relevant art that various modifications, additions, substitutions, and the like can be made without departing from the spirit of the invention, and these are therefore considered to be within the scope of the invention as defined in the following claims.

What is claimed is:

1. A collar for use in measuring vibrational response of a shaft, said collar comprising:
   first and second arcuate members;
   means for connecting said first arcuate member to said second arcuate member, said connected first and second arcuate members forming an outer collar circumference and having an inner circumference approximating an outer circumference of a shaft to be measured for vibrational response; and
   means for mounting multiple vibration responsive transducers on said connected first and second arcuate members; said connecting means including a bolt having two ends, at least one and being drilled, spot-faced and tapped; and said mounting means including said at least one drilled, spot-faced and tapped end.

2. The collar of claim 1 wherein said first and second arcuate members are equal-sized and an inner circumference of each arcuate member approximates 180° of the outer circumference of said shaft.

3. The collar of claim 1 wherein said means for connecting said first and second arcuate members comprises:
   a tab angled outward at each end of said first and second arcuate members, each tab having an aperture therein for receiving a bolt; and
   bolt and nut means for connecting two opposing tabs on said ends of said first and second arcuate members.

4. The collar of claim 1 wherein said means for mounting said multiple vibration responsive transducers comprises multiple drilled spot-faced tapped apertures in said connected first and second arcuate members.

5. The collar of claim 4 further comprising multiple vibration responsive transducers mounted in said apertures, each of said multiple vibration responsive transducers having a stud and each of said studs being inserted into one of said apertures.

6. The collar of claim 1 further comprising a vibration responsive transducer mounted into said one bolt end.

7. The collar of claim 6 wherein said vibration responsive transducer includes a stud, said stud being inserted into said drilled spot-faced and tapped one bolt end.

8. The collar of claim 1 further comprising means for mounting an input transducer on said connected first and second arcuate members.

9. The collar of claim 8 wherein said two ends of the bolt are drilled, spot-faced and tapped, and wherein said means for mounting said input transducer comprises at least one of said drilled, spot-faced and tapped ends of said bolt.

10. The collar of claim 9 further comprising an input transducer mounted in said drilled, spot-faced and tapped one bolt end.

11. The collar of claim 10 wherein said input transducer includes a stud, said stud being inserted into said drilled spot-faced and tapped one bolt end.

12. The collar of claim 10 wherein said input transducer comprises a tangential force input transducer.

13. The collar of claim 1 further comprising multiple vibration responsive output transducers mounted to said means for mounting multiple vibration responsive transducers.

14. The collar of claim 13 wherein at least one of said multiple vibration responsive output transducers comrpises an accelerometer.

15. The collar of claim 1, wherein both ends of said bolt are drilled, spot-faced and tapped.

16. A collar for use in measuring vibrational response of a shaft under test, said collar comprising:
   a first arcuate member having two ends and a second arcuate member having two ends;
   means for connecting said first arcuate member to the second arcuate member ends to ends, an inner circumference of said connected first and second arcuate members approximating an outer circumference of a shaft to be measured for vibrational response;
   means for mounting multiple vibration responsive output transducers on said connected first and second arcuate members;
   means for mounting an input transducer on said connected first and second arcuate members;
   multiple vibration responsive output transducers mounted to said means for mounting multiple vibration responsive output transducers; and
   an input transducer mounted to said means for mounting an input transducer;
   said means for connecting said first and second arcuate members comprising:
      a tab angled outward at each end of said first and second arcuate members, each tab having an aperture therein for receiving a bolt; and
      bolts and nut means for connecting pairs of opposing tabs on said ends of said first and second arcuate members, wherein each of said bolts is premounted to one of said opposing tabs and wherein a head of each of said bolts is drilled, spot-faced, and tapped;
   wherein said means for mounting said multiple vibration responsive output transducers comprises multiple drilled spot-faced tapped output apertures in said connected first and second arcuate members, and wherein said means for mounting said input transducer comprises a drilled spot-faced tapped input aperture in said connected first and second arcuate members; and
   wherein each of said multiple vibration responsive output transducers has a stud and said stud is inserted into a respective one of said output apertures, and wherein said input transducer has a stud and said stud is inserted into said input aperture.

17. A collar system for use in measuring vibrational response of an axially extending shaft under test, said collar system comprising a first collar and a second collar surrounding and contiguous with a shaft under test, said second collar being axially spaced from said first collar, each of said first and second collars comprising:
   a first arcuate member having two ends and a second arcuate member having two ends;
   means for connecting said first and second arcuate members, wherein when said first arcuate member is connected to said second arcuate member with said connecting means, an inner circumference of said connected first and second arcuate members approximates an outer circumference of a shaft to be measured for vibrational response; and means for mounting multiple vibration responsive output transducers on said connected first and second arcuate members.

18. The collar system of claim 17 wherein at least one of said first and second collars further comprises means for mounting an input transducer on said connected first and second arcuate members.

19. The collar system of claim 18 wherein said means for connecting said first and second arcuate members includes a bolt, said bolt having a drilled, spot-faced and tapped head, and wherein said means for mounting said input transducer comprises said drilled, spot-faced and tapped bolt head.

20. The collar system of claim 18 further comprising an input transducer mounted to said means for mounting an input transducer.

21. The collar system of claim 17 wherein said means for connecting said first and second arcuate members includes a bolt, said bolt having a drilled, spot-faced and tapped head, and wherein said means for mounting vibration responsive output transducers comprises said drilled, spot-faced and tapped bolt head.

22. The collar system of claim 17 further comprising multiple vibration responsive output transducers mounted to said means for mounting multiple vibration responsive output transducers.

23. A collar for use in measuring vibrational response of a shaft, said collar having an outer collar circumference, an inner circumference approximating an outer circumference of a shaft to be measured for vibrational response, and means for mounting multiple vibration responsive transducers, said means comprising:

first means for orienting at least one transducer in a first direction; and second means for orienting at least one transducer in a second direction that is substantially orthogonal to said first direction.

24. The collar of claim 23 wherein said first direction is a radial direction and said second direction is a tangential direction.

25. The collar of claim 24 wherein said first and second orienting means are disposed at substantially the same radial location about said outer collar circumference.

26. The collar of claim 25 wherein said means for mounting multiple vibration responsive transducer further comprises:

third means for orienting at least one transducer in a third direction that is substantially orthogonal to both said first and said second directions, said third orienting means being disposed at substantially the same radial location about said outer collar circumference as said first and second orienting means.

27. The collar of claim 24 wherein all transducers oriented in a common direction are disposed at equal radial intervals about said outer collar circumference.

28. The collar of claim 23 wherein said means for mounting multiple vibration responsive transducers comprises:

a plurality of support means disposed substantially symmetrically around said outer collar circumference.

29. The collar of claim 28 wherein each of said support means further comprises:

third means for orienting at least one transducer in a third direction that is substantially orthogonal to both said first and second directions.

30. The collar of claim 28 wherein each of said support means protrudes radially outward from said outer collar circumference a distance substantially greater than the radial thickness of either said first or second arcuate member.

31. The collar of claim 30 wherein each of said support means is substantially rectangular in shape and has at least two substantially planar faces, said first and second orienting means disposed one on each of said faces.

32. The collar of claim 30 wherein said first and second orienting means for each of said support means are disposed at substantially the same radial location about said outer collar circumference.

33. The collar of claim 28 comprising a radial output transducer and a tangential output transducer mounted to at least one of said support means.

34. The collar of claim 33 comprising an input transducer mounted to at least one of said support means.

35. The collar of claim 28 wherein each of said support means has a surface for mounting a radially-directed transducer slightly obliquely relative to a tangent of said outer collar circumference such that a center line drawn through the major axis of said radially-directed transducer passes through the center of said shaft.

36. The collar of claim 28 wherein said collar has substantial symmetry with respect to mass.

37. The collar of claim 36 wherein said collar has substantial symmetry with respect to stiffness.

38. The collar of claim 36 wherein said symmetry is with respect to each of a plurality of diameters through the approximate radial positions of each of said support means.

39. The collar of claim 23 wherein said collar is sufficiently rigid to substantially prevent vibrational noise caused by collar deformation or by relative motion between said collar and said shaft.

40. The collar of claim 23 comprising first and second arcuate members substantially equal-sized and wherein an inner circumference of each arcuate member approximates 180 degrees of the outer circumference of said shaft.

41. The collar of claim 23 comprising first and second arcuate members; and means for connecting said arcuate members comprising:
a first tapped aperture disposed on at least one end of either said first or second arcuate member; and
a connecting bolt having a threaded end sized to mate with said first tapped aperture.

42. The collar of claim 41 wherein a head of said connecting bolt has a tapped aperture for mating with a stud of a transducer.

43. The collar of claim 41 wherein the threaded end of said connecting bolt has a tapped aperture for mating with a stud of a transducer.

44. The collar of claim 41 wherein said first tapped aperture and a second tapped aperture are both disposed on opposite ends of one of said arcuate members, the other one of said arcuate members having a hole drilled fully through each of its ends, said hole being sized so that said connecting bolt passes through when said first and second arcuate members are connected.

45. The collar of claim 23 wherein said inner circumference is defined by interconnected first and second arcuate members, said inner circumference being slightly undersized relative to said outer shaft circumference so that a small gap exists between ends of said first and second arcuate members when fully connected.

46. A collar for use in measuring vibrational response of a shaft, said collar having an outer collar circumference, an inner circumference approximating an outer circumference of a shaft to be measured for vibrational response, and means for mounting multiple vibration responsive transducers thereon; said means further comprising means for orienting at least two transducers in a tangential direction relative to said outer collar circumference.

47. The collar of claim 46 wherein said collar has substantial symmetry with respect to mass.

48. The collar of claim 46 wherein all of said transducers oriented in a tangential direction are disposed at substantially the same radial distance from the center of said shaft.

49. The collar of claim 46 wherein all of said transducers oriented in a tangential direction are disposed to be in phase.

50. A collar for use in measuring vibrational response of a shaft, said collar having an outer collar circumference, an inner circumference approximating an outer circumference of a shaft to be measured for vibration response, and means for mounting at least one vibration responsive transducer in an axial direction relative to said outer collar circumference to measure vibrational response in said axial direction, said axial direction corresponding to a longitudinal axis of said shaft.

51. The collar of claim 50, further comprising a vibration responsive transducer disposed on said mounting means.

* * * * *

UNITED STATES PATENT AND TRADEMARK OFFICE
CERTIFICATE OF CORRECTION

PATENT NO.   : 5,520,061
DATED        : May 28, 1996
INVENTOR(S)  : Thibault et al.

It is certified that error appears in the above-indentified patent and that said Letters Patent is hereby corrected as shown below:

In the claims:

Column 17, line 24, substitute --end-- for "and".
Column 18, line 6, substitute --comprises-- for "comrpises".
Column 19, line 44, substitute --transducers-- for "transducer".
Column 21, line 1, insert --mounting-- between "said" and "means".

Signed and Sealed this

Eighth Day of October, 1996

Attest:

BRUCE LEHMAN

Attesting Officer    Commissioner of Patents and Trademarks